(12) United States Patent
Allersma et al.

(10) Patent No.: US 7,943,831 B2
(45) Date of Patent: May 17, 2011

(54) PMMOV RESISTANT CAPSICUM PLANTS

(75) Inventors: Anton Pieter Allersma, Hoek van Holland (NL); René Johannes M. Hofstede, Boven-Leeuwen (NL); Dirk Vreugdenhil, 's-Gravenzande (NL)

(73) Assignee: Monsanto Invest B.V., Amstelveen (NL)

( * ) Notice: Subject to any disclaimer, the term of this patent is extended or adjusted under 35 U.S.C. 154(b) by 0 days.

(21) Appl. No.: 11/694,134

(22) Filed: Mar. 30, 2007

(65) Prior Publication Data

US 2007/0234441 A1    Oct. 4, 2007

Related U.S. Application Data

(63) Continuation of application No. PCT/NL2005/000707, filed on Sep. 30, 2005.

(30) Foreign Application Priority Data

Oct. 1, 2004  (EP) .................................... 04077744
Oct. 6, 2004  (EP) .................................... 04077768

(51) Int. Cl.
*A01H 5/00*   (2006.01)
*A01H 5/10*   (2006.01)
*A01H 1/02*   (2006.01)
*A01H 1/00*   (2006.01)
*C12N 15/82*  (2006.01)

(52) U.S. Cl. ..................... 800/317.1; 800/260; 800/279; 800/288; 800/298; 800/295; 435/418; 435/419; 435/468

(58) Field of Classification Search .......................... None
See application file for complete search history.

(56) References Cited

U.S. PATENT DOCUMENTS 5,591,616 A    1/1997   Hiei et al. .................. 435/172.3

OTHER PUBLICATIONS

Boukema, "Resistance to a new strain of TMV in *Capsicum chacoense* Hunz," *Capsicum Newsletter*, 1:49-51 (1982).
Boukema, "Resistance to TMV in *Capsicum chacoense* Hunz. Is Governed by an Allele of the L-locus," *Capsicum Newsletter*, 3:47-48 (1984).
Boukema, "Male and Female Fertility in Interspecific crosses with *Capsicum chacoense* Hunz," *Capsicum Newsletter*, 3:54-55 (1984).
Chaim et al., "Identification of quantitative trai loci associated with resistance to cucumber mosaic virus in *Capsicum annuum*," *Theor. Appl. Genet.*, 102:1213-1220 (2001).
Lefebvre et al., "Towards the saturation of the pepper linkage map by alignment of three intraspecific maps including known-function genes," *Genome* 45(5):839-854 (2002).
Matsunaga et al., "DNA Markers Linked to Pepper Mild Mottle Virus (PMMoV) Resistant Locus ($L^4$) in *Capsicum*," *J. Japan. Soc. Hort. Sci.*, 72(3):218-220 (2003).

*Primary Examiner* — Medina A Ibrahim
(74) *Attorney, Agent, or Firm* — Banner & Witcoff, Ltd.

(57) ABSTRACT

The present invention relates to a plant of the *Capsicum* genus, which plant exhibits resistance to Pepper mild mottle virus (PMMoV) pathotype 1.2.3 due to the presence of the L4 resistance allele in the genome of said plant, wherein the genetic information responsible for the SNFD phenotype is absent from or is repressed in the genome of said plant at least to such an extent that the SNFD phenotype is not expressed. The present invention further relates to a method of producing a plant of the *Capsicum* genus that exhibits resistance to PMMoV pathotype 1.2.3, comprising the steps of a) providing a recipient plant of the *Capsicum* genus that is susceptible to PMMoV pathotype 1.2.3 or a part thereof, and b) introducing into the genome of said recipient plant or a part thereof or a progeny plant thereof a genomic region comprising a truncated L4 resistance allele, wherein said allele comprises genetic information capable of being expressed in said plant or plant part or progeny plant thereby conferring resistance to PMMoV pathotype 1.2.3 to said plant or plant part or progeny plant, and wherein genetic information that confers the SNFD phenotype is absent from said allele at least to such an extent that the SNFD phenotype is not expressed.

27 Claims, 3 Drawing Sheets

E63/M61-F-501
E66/M43-F-387
E66/M49-F-387
E66/M61-F-99
E67/M50-F150
E67/M62-F-214
E70/M54-F-133
E71/M47-F-550
E74/M61-F-385

Group 1/3

Group 3     Group 1     Group 2

E60/M54-F-447    E39/M58-F-95    E35/M49-F-90
                     E54/M55-F-101   E39/M58-F-65
                     E58/M60-F-255   E39/M51-F-380
                     E58/M50-F-580   E58/M62-F-168
                                       E66/M54-F-600
                                       Tm3-DRS

| Group 1 | Sequence 1st primer (5'-3') | Sequence 2nd primer (5'-3') | Marker length (bp) |
|---|---|---|---|
| E39/M58-F-95 | GACTGCGTACCAATTCAGA (SEQ ID NO:5) | GATGAGTCCTGAGTAACGT (SEQ ID NO:8) | 95 |
| E54/M55-F-101 | GACTGCGTACCAATTCCCT (SEQ ID NO:6) | GATGAGTCCTGAGTAACGA (SEQ ID NO:9) | 101 |
| E58/M60-F-255 | GACTGCGTACCAATTCCGT (SEQ ID NO:7) | GATGAGTCCTGAGTAACTC (SEQ ID NO:10) | 255 |
| E58/M50-F-580 | GACTGCGTACCAATTCCGT (SEQ ID NO:7) | GATGAGTCCTGAGTAACAT (SEQ ID NO:11) | 580 |
| Group 2 | Sequence 1st primer (5'-3') | Sequence 2nd primer (5'-3') | Marker length (bp) |
| E35/M49-F-90 | GACTGCGTACCAATTCACA (SEQ ID NO:12) | GATGAGTCCTGAGTAACAG (SEQ ID NO:16) | 90 |
| E39/M58-F-65 | GACTGCGTACCAATTCAGA (SEQ ID NO:13) | GATGAGTCCTGAGTAACGT (SEQ ID NO:17) | 65 |
| E39/M51-F-380 | GACTGCGTACCAATTCAGA (SEQ ID NO:13) | GATGAGTCCTGAGTAACCA (SEQ ID NO:18) | 380 |
| E58/M62-F-168 | GACTGCGTACCAATTCCGT (SEQ ID NO:7) | GATGAGTCCTGAGTAACTT (SEQ ID NO:19) | 168 |
| E66/M54-F-600 | GACTGCGTACCAATTCGAT (SEQ ID NO:14) | GATGAGTCCTGAGTAACCT (SEQ ID NO:20) | 600 |
| Tm3-DRS | AATCCTTCAACTGCCATTTC (SEQ ID NO:3) | ATTGGGACATGAGCTGTGTA (SEQ ID NO:21) | 350 |
| Group 3 | Sequence 1st primer (5'-3') | Sequence 2nd primer (5'-3') | Marker length (bp) |
| E60/M54-F-447 | GACTGCGTACCAATTCCTC (SEQ ID NO:22) | GATGAGTCCTGAGTAACCT (SEQ ID NO:20) | 447 |
| Group 1/3 | Sequence 1st primer (5'-3') | Sequence 2nd primer (5'-3') | Marker length (bp) |
| E63/M61-F-501 | GACTGCGTACCAATTCGAA (SEQ ID NO:23) | GATGAGTCCTGAGTAACTG (SEQ ID NO:28) | 501 |
| E66/M43-F-387 | GACTGCGTACCAATTCGAT (SEQ ID NO:14) | GATGAGTCCTGAGTAAATA (SEQ ID NO:29) | 387 |
| E66/M49-F-387 | GACTGCGTACCAATTCGAT (SEQ ID NO:14) | GATGAGTCCTGAGTAACAG (SEQ ID NO:16) | 387 |
| E66/M61-F-99 | GACTGCGTACCAATTCGAT (SEQ ID NO:14) | GATGAGTCCTGAGTAACTG (SEQ ID NO:28) | 99 |
| E67/M50-F-150 | GACTGCGTACCAATTCGCA (SEQ ID NO:24) | GATGAGTCCTGAGTAACAT (SEQ ID NO:11) | 150 |
| E67/M62-F-214 | GACTGCGTACCAATTCGCA (SEQ ID NO:24) | GATGAGTCCTGAGTAACTT (SEQ ID NO:19) | 214 |
| E70/M54-F-133 | GACTGCGTACCAATTCGCT (SEQ ID NO:25) | GATGAGTCCTGAGTAACCT (SEQ ID NO:20) | 133 |
| E71/M47-F-550 | GACTGCGTACCAATTCGGA (SEQ ID NO:26) | GATGAGTCCTGAGTAACAA (SEQ ID NO:30) | 550 |
| E74/M61-F-385 | GACTGCGTACCAATTCGGT (SEQ ID NO:27) | GATGAGTCCTGAGTAACTG (SEQ ID NO:28) | 385 |

Substitute Figure 3

PMMOV RESISTANT CAPSICUM PLANTS

RELATED APPLICATIONS

This application claims priority from PCT application number PCT/NL2005/000707, designating the United States and filed Sep. 30, 2005; which claims the benefit of the filing date of European application no. 04077768.2, filed Oct. 6, 2004; and of European application no. 04077744.3, filed Oct. 1, 2004; all of which are hereby incorporated herein by reference in their entirety for all purposes.

FIELD OF THE INVENTION

The present invention relates to disease-resistant plants. More specifically, the present invention relates to pepper plants that are resistant to specific pathotypes of Pepper mild mottle virus (PMMoV) and to methods of producing such plants.

BACKGROUND OF THE INVENTION

*Capsicum* (Solanaceae or nightshade family) is a genus of plants, of which the sweet and aromatic fruits are used as a spice, a vegetable, and a medicine. The genus comprises about 40 species. Most varieties contain capsaicin (methyl vanillyl nonenamide), a pungent chemical that produces a strong burning sensation in the mouth and that can be used as a circulatory stimulant and pain reliever in medicine. The plants originate in Central and South America, but since they tolerate nearly every climate, the fruits are produced all over the world. Commercial peppers are primarily of the species *Capsicum annuum* (bell pepper, cayenne pepper, Jalapeño pepper, Anaheim pepper), *Capsicum frutescens* (Tabasco pepper) and *Capsicum chinense* (Habañero pepper).

*Capsicum annuum*, also known as paprika or pimento, is an herbaceous annual species with fruits that vary in length, color and pungency, depending upon the cultivar. The species is cultivated world-wide, for example in Western Europe and the United States of America (USA). *Capsicum frutescens* and *C. chinense* have small extremely pungent fruit and are used in tabascos and other hot pepper products. Since a fairly warm climate is necessary for a strong aroma, the species are cultivated primarily in tropical regions and in warmer regions of the USA.

Vegetable crops of *Capsicum* spp. are damaged by many Tobamoviruses during cultivation. The genus Tobamovirus includes the type species Tobacco mosaic virus (TMV), and the serologically related Tomato mosaic virus (ToMV), Pepper mild mottle virus (PMMoV) and several other plant viruses. The viral infections can reduce the plant's vigor but do not commonly kill it. TMV, for instance, which affects a wide range of plants, including pepper, tomato and eggplant, causes severe necrosis on pepper fruits leaving most of the fruits unmarketable. TMV is a highly persistent disease because it can remain viable in soil for many years.

PMMoV systemically infects all *Capsicum* spp., including cultivars that are resistant to TMV and ToMV. Symptoms of the disease in bell pepper plants include stunting of young plants, crinkling and yellow mottling of leaves. Fruits are malformed (lumpy and mottled) and slightly reduced in size.

In 1980 a viral strain of a TMV-like virus (tm-3) was isolated that could infect the PMMoV-resistant *Capsicum* lines known at that time (Boukema et al., 1980). The isolated strain was called strain P14 of TMV. Following the discovery of strain P14, a line of the plant species *C. chacoense* (line PI 260429) was found in 1982 that exhibited resistance to this new virus (Boukema, 1982). It was later determined that the resistance in this plant was conferred by the L4 allele of the L-locus (Boukema, 1984) and that strain P14 was able to overcome the former resistance conferred by the L3 allele, whereas it could not break the resistance conferred by the L4 allele. This L3-conferred resistance-breaking strain, originally classified as TMV, was later reclassified as a specific PMMoV pathotype and the pathotype was assigned pathotype 1.2.3.

Amongst breeders, the *C. chacoense* line that exhibits resistance to PMMoV pathotype 1.2.3 as well as commercial pepper lines derived thereof, are commonly referred to as Tm3-resistant lines. Many breeding companies have since introgressed genetic material of this *C. chacoense* line comprising the L4 allele into their breeding lines in order to obtain resistant pepper plants with commercially favourable characteristics.

It is now known that the L4 allele confers resistance to a number of viruses, including ToMV, TMV, and to the PMMoV pathotypes 1, 1.2, and 1.2.3. The resistance conferred by the L4 allele is hereinafter termed "PMMoV resistance", although strictly speaking it confers broader resistance, as described above.

The nomenclature of Tobamoviruses has been the subject to several revisions in the period between 1980 and 2004. Herein, use is made of the nomenclature of the "Guidelines for the conduct of Tests for Distinctness, Uniformity and Stability" (TG/76/7) for sweet Pepper (*C. annuum* L.) issued by the Union for the Protection of New Varieties of Plants (UPOV) on Apr. 11, 1994. In these guidelines the genetic resistance to pepper Tobamovirus pathotypes is considered to be controlled by 5 alleles ($L^-$, $L^1$, $L^2$, $L^3$, and $L^4$) located on the same locus (L-locus). Reference is herein explicitly made to the Table on pp. 21-22 of the above-referred UPOV guideline TG/76/7, wherein the relationship is shown between resistance against the various virus pathotypes and the resistance-conferring allelic compositions in pepper. A homozygous $L^3L^3$ genotype of *C. annuum* confers resistance to Tobacco Mosaic Virus (TMV), Tomato Mosaic Virus (ToMV), Bell Pepper Mosaic Virus (BePMV), Tobacco Mild Green Mosaic Virus (TMGMV), Dulcamara Yellow Fleck Virus (DYFV), and Pepper Mild Mottle Virus (PMMoV) pathotype 1.2, whereas the homozygous $L^4L^4$ genotype provides an additional resistance to Pepper Mild Mottle Virus (PMMoV) pathotype 1.2.3.

The UPOV nomenclature differs somewhat from the nomenclature usually employed in the scientific literature on virology. Generally in the scientific literature nomenclature is confined to the species name and the designation of the isolate. The pathotype designation is only very occasionally described. For instance, the pathotype 1.2.3 of PMMoV is not incorporated in The Universal Virus Database of the International Committee on Taxonomy of Viruses (ICTV). It should further be noted that with respect to nomenclature and the developments therein over time, a given Tobamovirus may have acquired two or more trivial names and may have been further reclassified as explained in more detail below. It is to be understood that irrespective of any new assignment of a viral isolate, the present invention relates to resistance of plants to any viral strain that is conferred by the L4 allele.

Is indicated above, the resistance of *Capsicum* spp. to Tobamoviruses is conferred by pathotype-specific alleles (L1, L2, L3, L4) of the L-gene, and resistance to PMMoV pathotype 1.2.3 is conferred by the L4 allele. The region where the L-locus is located is positioned on the telomere of chromosome 11 south (Lefebvre et al, 2002). The resistance alleles act via triggering of the hypersensitive response (HR).

A remarkable and undesired characteristic of the resistance conferred by the L4 allele when introgressed from *C. chacoense* into other *Capsicum* species, is that the resistance in the new plant lines is inherited non-Mendelian. Mendel's law of segregation states that allele pairs segregate during gamete formation, and randomly unite at fertilization. For each character, a diploid organism inherits two alleles, one from each parent. If the two alleles differ, then one, the dominant allele, is fully expressed in the organism's phenotype; the other, recessive allele has no noticeable effect on the phenotype. According to normal Mendelian inheritance, the cross of a plant with a homozygous dominant allele and a plant with a homozygous recessive allele will result in an $F_1$, or first filial population, that is uniform, both genetically (whole population is heterozygous) as well as phenotypically (whole population expresses dominant trait). Such an $F_1$ population is said to be non-segregating for that dominant trait (of course in the $F_2$ population segregation will occur). Thus, an $F_1$ population does not segregate for a dominant trait when at least one of the parents is homozygous for that trait. Likewise, the presence of a non-segregating $F_1$ confirms the homozygosity of a dominant trait in one of a parent lines. This is however not the case with commercial plant lines in which the L4 allele is introgressed.

For plant breeders it is important that breeding lines are homozygous (true breeding), because the result of the breeding should preferably be predictable. When, for instance, a commercial hybrid is produced from two (homozygous) inbred lines, the resulting heterozygous $F_1$ plants are fitter than their inbred parents as a result of hybrid vigor or heterosis. Plant breeders purposely exploit such heterotic crosses to generate more robust progeny and the homozygous inbred lines serve as producer lines with high economic value. In breeding practice therefore, it is customary to assess whether a plant line is homozygous for a dominant resistance trait conferred by a single gene (i.e., a monogenic dominant trait) by selfing that plant line and screening its offspring for non-segregation. Alternatively an expected homozygous dominant plant line can be crossed with a homozygous recessive line whereby a segregating $F_1$ reveals that the tested "dominant" parent is not homozygous.

The L4 resistance allele is believed to be a normal monogenic dominant resistance allele (Boukema, 1983; Van Duin, 1998). However, in the case of the PMMoV-resistance conferred by the L4 resistance allele, breeders generally observe problems with the predictability of crosses from homozygous lines and the stability of those lines. Whereas the selfing of an expected homozygous (L4L4) resistant plant invariably results in an offspring with a uniform resistant phenotype (thereby confirming the homozygosity of the parent plant), the crossing, on the other hand, of such a homozygous resistant parent plant with a susceptible parent plant (i.e. one that lacks the L4 allele) often results in an $F_1$ comprising both resistant and susceptible plants, i.e. in a segregating $F_1$. The susceptibility of the plants may for instance be detected by the presence of systemic mosaic after inoculation with PMMoV pathotype 1.2.3. This phenomenon, wherein resistance is surprisingly lost in some of the $F_1$ offspring plants, is very inconvenient to breeders for reasons outline above. Breeders often refer to such unpredictable homozygous parent plants as "segregating" plants, although strictly speaking, their $F_1$ offspring is segregating.

In the development of improved PMMoV-resistant inbred lines, and by using conventional plant selection and test crossings, breeders have recently shown to be able to obtain homozygous plants that produce a normal non-segregating $F_1$, (i.e., one that follows Mendel's law), thereby having fixed the resistance conferred by the L4 allele in that line. It is at present unclear how this was achieved. A major problem of these "non-segregating" plants is, however, that they exhibit reduced fertility and dwarf growth. An important consequence of the reduced fertility is that such plants produce limited amounts of seed and/or limited amount of pollen. Thus, although such plants are resistant and "non-segregating", they exhibit a phenotype characterized by a low fertility and dwarf growth that is undesired for commercial seed production. The dwarf growth may for instance be indicated by late ripening of the seed (i.e. slow growth) or by reduced (rate of) development of the plant. This phenotype will be further designated in this application as an "SNFD phenotype", for Segregating Non-Fertile Dwarf. There is at present no explanation for the association between these negative traits, which include problems with growth, fertility and sterility, and the introgression of the L4 allele from *C. chacoense* into other *Capsicum* lines (vide, e.g. Van Duin, 1998).

The introgression of any of the L1, L2 and L3 alleles of the L-gene into *Capsicum* spp. have always been found to produce Mendelian inherited populations without showing the SNFD phenotype in homozygous resistant plants. The L4 introgression from *C. chacoense* now for the first time gives rise to the above problems.

At present there is a need for pepper plants that are resistant to PMMoV pathotype 1.2.3 as conferred by the L4 allele, that are "non-segregating", that show normal (rates of) development and that produce proper amounts of seed. It is therefore an object of the present invention to provide plants of the genus *Capsicum*, which combine resistance to PMMoV pathotype 1.2.3 as conferred by the L4 allele with agronomically or commercially good traits, such as good growth and normal seed production, thus without the undesired characteristics of the SNFD phenotype.

SUMMARY OF THE INVENTION

This object is achieved by the present invention. According to the invention it has been found that it is possible to break the link between the resistance to PMMoV pathotype 1.2.3 and the SNFD phenotype, observed in homozygous plants as described above, by reducing the size of the genomic introgression that comprises the L4 allele. In particular, this is achieved by the removal of genetic information from the L4 resistance allele that lies in the direct vicinity of the PMMoV-resistance-conferring part of the L4 allele. The result thereof is that the resistance to PMMoV pathotype 1.2.3 may be transferred from one plant to another without the transfer of the SNFD phenotype-conferring part and it has thereby become possible to produce PMMoV-resistant and agronomically valuable plants that do not exhibit the SNFD phenotype.

Without wishing to be bound by theory, it is believed that the negative side-effects characteristic of the SNFD phenotype are caused by the *C. chacoense* chromosome fragment on which the L4 allele is situated, and that when the *C. chacoense* chromosome fragment is inserted in for instance a *C. annuum* genome, the SNFD phenotype is caused by recessive genes in the vicinity of the resistance-conferring part of the L4 allele that are genetically linked to the L4 allele itself and disrupt the chromosomal organisation of the recipient plant's genome. Therefore, the SNFD phenotype is expressed only in plants that are homozygous for the *C. chacoense* chromosomal introgression of the complete L4 allele.

Now that this important insight on the possibility to break the link between the desired and undesired phenotypes conferred by the L4 allele has been gained, it has become possible to select plants in which the genetic information for the SNFD phenotype is removed from the vicinity of the resistance-conferring part of the L4 allele or changed to such an extent that in homozygous plants the SNFD phenotype is no longer expressed in combination therewith.

The present invention now provides in a first aspect a plant of the *Capsicum* genus that exhibits resistance to Pepper mild mottle virus (PMMoV) pathotype 1.2.3 due to the presence of the L4 resistance allele in the genome of said plant, wherein said L4 allele is truncated. The truncation provides an allele of reduced length and results in non-segregating plants that are fertile and exhibit normal growth, i.e. the absence of the SNFD phenotype.

The absence of the genetic information responsible for the SNFD phenotype may be effected by removal or change of the genetic information in the vicinity of the L4 allele that results in the SNFD phenotype and is preferably brought about by recombination event(s) in the vicinity of the L4 allele. When the SNFD information is present only on one side of the allele, a single recombination event is sufficient to remove this information. When the genetic information for the SNFD phenotype lies on both sides of the resistance allele, both parts of this genetic information are preferably changed or removed. According to a preferred embodiment of the invention, plants are selected wherein at least one recombination event has taken place, preferably a recombination event on the north side (centromeric side) of the L4 allele on the south side of chromosome 11, although truncations on the telomeric side are also possible. In the case of a double recombination, the recombination events do not need to have taken place in one generation, but recombination events from successive generations may together result in the eventual removal or change of the genetic information on one or both sides of the resistance allele. The at least one recombination event should be performed such that genetic information responsible for conferring the resistance is not removed, thereby maintaining the presence of the resistance-conferring part of the L4 resistance allele.

In a preferred embodiment of a plant of the present invention said L4 resistance allele is derived from the genome of *C. chacoense*.

In order to assess whether the appropriate genetic information is removed or changed, the skilled person may appropriately make use of genetic markers. The present invention now describes several genetic markers that may be used in, for instance, marker-assisted selection of recombinant plants. Such use is well known in the art and will be described in more detail below.

In a preferred embodiment, the present invention provides a plant wherein the genetic information responsible for the SNFD phenotype is absent as indicated by the absence of at least one marker linked to the L4 resistance allele, wherein said marker is selected from the group consisting of Group 2 markers (E35/M49-F-90, E39/M58-F-65, E39/M51-F-380, E58/M62-F-168, E66/M54-F-600 and Tm3-DRS), Group 3 markers (E60/M54-F-447) and Group 1/3 markers (E63/M61-F-501, E66/M43-F-387, E66/M49-F-387, E66/M61-F-99, E67/M50-F-150, E67/M62-F-214, E70/M54-F-133, E71/M47-F-550, E74/M61-F-385), preferably Group 3 and Group 2 markers, more preferably Group 2 markers (E35/M49-F-90, E39/M58-F-65, E39/M51-F-380, E58/M62-F-168, E66/M54-F-600 and Tm3-DRS).

In another preferred embodiment the present invention provides a plant wherein the presence of the L4 resistance allele is indicated by the presence of at least one marker linked to the L4 resistance allele selected from the markers of Group 1 (E58/M50-F-580, E39/M58-F-95, E58/M60-F-255 and E54/M55-F-101), and Group 1/3 (E63/M61-F-501, E66/M43-F-387, E66/M49-F-387, E66/M61-F-99, E67/M50-F-150, E67/M62-F-214, E70/M54-F-133, E71/M47-F-550, E74/M61-F-385), preferably selected from Group 1 markers, more preferably selected from the markers E58/M50-F-580 and E54/M55-F-101.

The markers mentioned above are based on AFLP-primers that consist of "core primers" (5'-GACTGCGTACCAATTC-3' (SEQ ID NO:1) and 5'-GATGAGTCCTGAGTAA-3' (SEQ ID NO:2)), corresponding with the restriction sites of the restriction enzymes EcoRI (coded E) and MseI (coded M), respectively, plus three additional selective nucleotides, which are indicated by a primer code. Primer codes can be found at the Worldwide Website: keygene.com/publications/index.htm and specifically in the document entitled "KF Nomenclature Primer Enzyme Combinations.pdf" disclosed there. The size of the amplified fragment (in base pairs) is noted after the primer enzyme combination. For example marker E58/M60-255 indicates an amplified fragment of 255 base pairs, achieved after cutting DNA with the primer enzyme combination [EcoRI+primer code 58/MseI+primer code 60].

The primer codes are as follows: 35:ACA; 39:AGA; 43:ATA; 47:CAA; 49:CAG; 50:CAT; 51:CCA; 54:CCT; 55:CGA; 58:CGT; 60:CTC; 61:CTG; 62:CTT; 63:GAA; 66:GAT; 67:GCA; 70:GCT; 71:GGA; 74:GGT. An example for primer enzyme combination code E63/M61-F-501 is: EcoRI+GAA (=E63)/MseI+CTG (=M61).

Marker Tm3-DRS, derived from marker TG036 (Lefebvre et al., 2002) is a marker defined by the PCR primer pair P118 (sequence 5'-AATCCTTCAACTGCCATTTC-3' (SEQ ID NO:3)) and primer P119 (sequence 5'-ATTGGGACATGAGGTGTGTA-3' (SEQ ID NO:4)) and can be detected by performing a PCR with primers P118 and primer P119, after which the PCR-product is digested with Tru1I (restriction site TTAA). The presence of an amplified fragment of approximately 350 base pairs indicates the presence of the L4 allele.

The provision of a plant wherein the genetic information responsible for the SNFD phenotype is absent or removed may also be described in terms of providing a plant with a truncated L4 allele as described in more detail below. The aspects relating to such truncation apply similarly to the removal or change of the genetic information as described above.

In another preferred embodiment of a plant of the invention, the plant is a plant of the species *C. annuum*.

In still another preferred embodiment of the plant of the invention, the plant is homozygous for the L4 resistance allele, and the homozygous plant is preferably an inbred plant.

In another aspect, the present invention provides a plant of the *Capsicum* genus that exhibits resistance to Pepper mild mottle virus (PMMoV) pathotype 1.2.3 due to the presence of the L4 resistance allele in the genome of said plant, wherein said L4 allele is truncated, and wherein said truncation comprises the removal of nucleotide sequences over a genetic distance of about 0.001 to 10 cM from the telomeric and/or centromeric side, preferably 0.001 to 10 cM from the centromeric side of the allele. The preferred embodiments as described above also apply for the plant of according to this aspect of the invention.

The observed recombination frequency between markers of Group 1, comprising the core TM-3 resistance gene(s), and markers of group 3 was equivalent to a distance of about 2 cM. The observed recombination frequency between markers of Group 1 and markers of group 2 was also equivalent to a distance of about 2 cM. No distance could be determined between any of the markers within the marker Groups identified herein due to the absence of recombination. Thus, a truncation as described herein preferably represents a genetic deletion over a distance of less than 2 cM from any of the markers located centromeric (Group 2) or telomeric (Group 3) from the location of any of the Group 1 markers.

In another aspect, the present invention provides a hybrid pepper plant that exhibits resistance to PMMoV pathotype 1.2.3, obtainable by crossing a homozygous, preferably inbred, plant of the present invention with another homozygous, preferably inbred, pepper plant that exhibits commercially desirable characteristics.

In yet another aspect, the present invention provides an isolated nucleic acid sequence comprising a truncated L4 resistance allele, wherein said truncated L4 resistance allele comprises genetic information capable of being expressed in a plant of the *Capsicum* genus thereby conferring resistance to PMMoV pathotype 1.2.3 to said plant, and wherein genetic information that confers the SNFD phenotype is absent from said allele.

In a preferred embodiment of such an isolated nucleic acid sequence the resistance-conferring genetic information comprises at least one marker selected from the group comprising markers E39/M58-F-95, E54/M55-F-101, E58/M60-F-255 and E58/M50-F-580, preferably selected from the group consisting of the markers E39/M58-F-95, E54/M55-F-101, E58/M60-F-255 and E58/M50-F-580, more preferably at least one marker selected from the group consisting of markers E54/M55-F-101 and E58/M50-F-580, and the resistance-conferring genetic information further comprises the genetic information that confers the SNFD phenotype and comprises the absence from said L4 resistance allele of at least one marker selected from the group consisting of Group 2 markers and Group 3 markers, preferably Group 2 markers. In a most preferred embodiment, the L4 resistance allele comprised in the isolated nucleic acid sequence of the invention is derived from the genome of *C. chacoense*.

In another aspect, the present invention provides a method of producing a plant of the *Capsicum* genus that exhibits resistance to PMMoV pathotype 1.2.3, comprising the steps of a) providing a recipient plant of the *Capsicum* genus that is susceptible to PMMoV pathotype 1.2.3 or a part thereof, and b) introducing into the genome of said recipient plant or a part thereof or a progeny plant thereof a genomic region comprising a truncated L4 resistance allele, wherein said allele comprises genetic information capable of being expressed in said plant or plant part or progeny plant thereby conferring resistance to PMMoV pathotype 1.2.3 to said plant or plant part or progeny plant, and wherein genetic information that confers the SNFD phenotype is absent from said allele at least to such an extent that the SNFD phenotype is not expressed. Step b) may be preceded by providing said genomic region comprising a truncated L4 resistance allele, for instance in the form of a recombinant donor plant having a truncated form of the L4 resistance allele as described herein, or in the form of a vector comprising said genomic region as an insert.

A genomic region comprising a truncated L4 resistance allele used in a method of the present invention comprises an L4 resistance allele of which the size is reduced as compared to the L4 allele that results in plants having the SNFD phenotype. The size of the L4 resistance allele is reduced such that the reduction in size does not affect the genetic information responsible for conferring the resistance to PMMoV pathotype 1.2.3.

A very suitable method for realizing the introduction of the genomic region comprising a truncated L4 resistance allele is performed by genome introgression in a progeny plant derived from a cross between the recipient plant and a PMMoV pathotype 1.2.3-resistant donor plant of the *Capsicum* genus that comprises an L4 resistance allele. The process of introgression is well known to the skilled person and generally involves the introduction of one or more genes of one species into the gene pool of another through repeated backcrossing of an interspecific hybrid with one of its parents.

The skilled person will readily understand that introgression is however not the sole manner in which the L4 resistance allele or a genomic region comprising the L4 resistance allele can be introduced in the genome of a plant. Other methods may for instance involve the use of transgenic techniques, such as haploid cell fusion, plant transformation and the like. The introduction of said genomic region may therefore also be performed by in vitro culture techniques, by protoplast fusion, by transformation or by a doubled haploid technique. Often, such techniques are not performed with intact plants but with plant parts, in general reproduction material of said plant, such as tissue cultures of single cells or protoplasts. Therefore, in order to obtain a plant of the invention such methods may optionally include a further step of growing said plant part into a pepper plant. Generally this will involve regenerating plants or reproduction material of said plants or both from the plant part or tissue transformed with heterologous DNA and, optionally, biologically replicating said plants or reproduction material or both.

A method of the present invention wherein a truncated L4 resistance allele is introduced into a recipient plant of the *Capsicum* genus by the process of introgression preferably results in a progeny plant having introgressed into its genome a genomic region comprising a truncated L4 resistance allele. Since the process of obtaining progeny plants with truncated L4 resistance alleles involves recombination, it is preferred that a segregating population is produced prior to performing any selections based on either phenotype or genotype of progeny plants. Therefore, the progeny plant to be produced and having in its genome a truncated L4 resistance gene is preferably a plant of a segregating population, for instance produced by self-pollination of an $F_1$ plant obtained from the above mentioned cross, or by crossing an $F_1$ plant obtained from said cross with another pepper plant.

In methods of the invention, the genomic region is preferably introduced from the genome of *C. chacoense* and the recipient plant used in such methods is preferably a *C. annuum* plant.

Although the basic elements of a method of producing a plant of the invention have now been described, a method of the invention may comprise additional steps. In a preferred embodiment, a method of the invention further comprises the steps of c) selecting a PMMoV pathotype 1.2.3-resistant plant or PMMoV pathotype 1.2.3-resistant progeny plant thereof, and d) selecting a resistant plant or resistant progeny plant that does not express the SNFD phenotype.

The step of selecting a PMMoV pathotype 1.2.3-resistant plant or progeny plant may be performed by methods based on phenotypic determination, such as by using a resistance bioassay, for instance by inoculating a leave of the plant with a suspension of PMMoV pathotype 1.2.3 and assessing the occurrence of infection. In preferred embodiments however, the step of selecting a PMMoV pathotype 1.2.3-resistant plant comprises the process of screening the genome of said plant or progeny plant for the presence of at least one marker of the L4 resistance allele selected from the group comprising markers of Group 1 or of Group 1/3 indicative of the presence of the resistance-conferring part of the L4 allele in said plant. Suitable markers of Group 1 include markers E39/M58-F-95, E54/M55-F-101, E58/M60-F-255 and E58/M50-F-580, preferably the presence of at least one marker selected from the group consisting of markers E54/M55-F-101 and E58/M50-F-580 is determined. Markers of Group 1/3 suitable for assessing the presence of the resistance trait include those markers of which the skilled person has established the presence in resistant plants. The markers of Group 1/3 both comprise markers that indicate the L4 resistance allele as well as markers that indicate the SNFD phenotype-conferring parts in that allele. Thus, some Group 1/3 markers indicate a suitable truncation that removes the SNFD phenotype-conferring parts in the L4 resistance allele and which are analogous to the Group 3 markers, while other Group 1/3 markers indicate the presence of the core resistance genes or regulatory sequences therefore which are analogous to the Group 1 markers.

The step of selecting from amongst said a PMMoV pathotype 1.2.3-resistant plants a plant or progeny plant that does not express the SNFD phenotype (above described step d) constitutes the core of the marker-assisted breeding process disclosed by the present invention. The selection of a resistant plant or progeny plant that does not express the SNFD phenotype preferably comprises the screening of the truncated L4 resistance allele in the genome of the resistant plant or progeny plant for at least one marker of the L4 resistance allele selected from the group consisting of Group 2 markers and Group 3 markers (optionally also selected from Group 1/3 markers), preferably Group 2 markers, and selecting a plant or progeny plant wherein at least one of said markers is absent thereby indicating the truncation.

In another aspect, the present invention provides a method for producing an inbred plant of the *Capsicum* genus that exhibits resistance to PMMoV pathotype 1.2.3, comprising performing a method of producing a plant of the *Capsicum* genus that exhibits resistance to PMMoV pathotype 1.2.3 as described above and further performing the steps of: e) selfing the selected plants; f) planting seed obtained from said selfing and growing said seed into plants; g) identifying plants from step g) that exhibit PMMoV pathotype 1.2.3 resistance and possess commercially desirable characteristics, and h) repeating steps e)-g) until an inbred pepper plant is produced that exhibits PMMoV pathotype 1.2.3 resistance and possesses commercially desirable characteristics. Commercially desirable characteristics in the context of the present invention may relate to any characteristic such as a fruit characteristics like for instance an improved appearance, a higher seed yield, improved fertility, a higher fruit yield, a larger or smaller fruit, or an improved fruit color or taste; or for instance to such characteristics as an improved stem strength, an improved root system, improved stress resistance, improved disease resistance, etc. In practice, a commercially desirable characteristic may be any characteristic that will make the plant commercially more valuable over a wild-type plant.

In another aspect, the present invention provides a plant or inbred plant of the *Capsicum* genus that exhibits resistance to PMMoV pathotype 1.2.3 obtainable by any one of the methods of to the invention described above.

In other aspects the present invention relates to progeny of a plant according to the invention, to parts such as leaves, stems, roots, root tips, rootstocks, shoots, fruits and the like or parts such as cells, protoplasts, calli, cell clumps, (somatic) embryos, anthers, petioles, pollen, ovules, flowers, cells in culture, seeds and the like of a plant according to the invention. Such parts may be suitable for propagation, preferably by (organ) tissue culture, or they may be suitable for consumption, such as a fruit.

In another aspect, the present invention provides a pepper seed produced by growing a pepper plant of the invention.

In another aspect, the present invention provides a hybrid pepper plant, or part thereof, that exhibits resistance to PMMoV pathotype 1.2.3, obtainable by crossing an inbred pepper plant of the present invention obtainable by a method of the invention with, preferably, an inbred pepper plant that exhibits commercially desirable characteristics.

BRIEF DESCRIPTION OF THE DRAWINGS

FIG. 3 provides detailed information on the markers as used herein and in particular the nucleotide sequence information and marker length. The marker length is the approximate length in base pairs of a DNA fragment amplified by carrying out a PCR reaction with the indicated primers using genomic DNA isolated from *C. chacoense* accession PI 260429 as template DNA.

DETAILED DESCRIPTION OF THE INVENTION

Definitions

Figure 1:
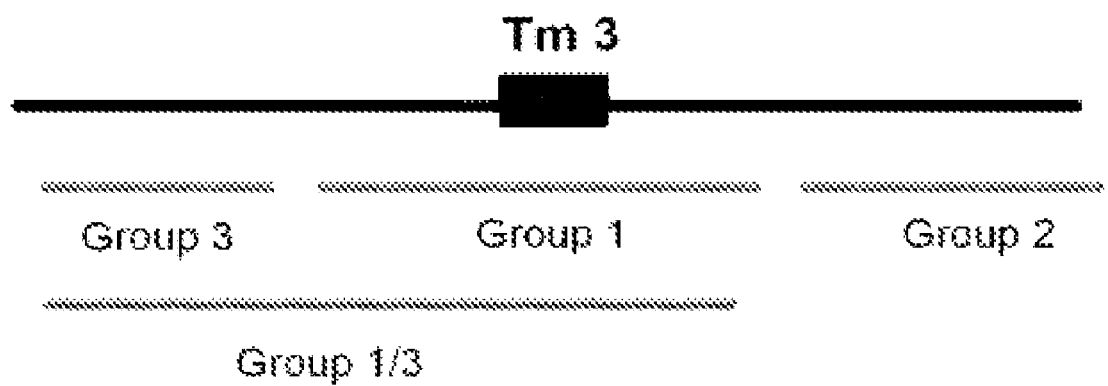
FIG. 1 shows the micromap of the L4 locus indicating different groups (Group 1, 2, 3, 1/3) of markers, linked to this locus Markers present within each of these groups are listed in Table 1 as shown in Example 1.

The headings provided herein are not limitations of the various aspects or embodiments of the invention that can be had by reference to the specification as a whole. Accordingly, the terms defined immediately below are more fully defined by reference to the specification as a whole.

The term "L4 resistance allele" or "L4 allele" is used herein to refer to the pathotype-specific resistance allele of the L-gene of *Capsicum* spp. that provides these plants with resistance to Tomato mosaic virus (ToMV) and Pepper mild mottle virus (PMMoV) pathotypes 1, 1.2, and 1.2.3. as first described by Boukema (1984) and which gene is part of the L-locus. The region where the L-locus is located is positioned on the telomere of chromosome 11 south. The L4 allele in non-truncated form associates with marker Tm3-DRS. The L4 allele therefore represents a nucleotide sequence, e.g. derivable from *C. chacoense* accession PI 260429, bordered by one or more Group 2 markers as defined herein (E35/M49-F-90, E39/M58-F-65, E39/M51-F-380, E58/M62-F-168, E66/M54-F-600 and Tm3-DRS) and one or more Group 3 or Group 1/3 markers (E60-M54-F-447, E63/M61-F-501, E66/M43-F-387, E66/M49-F-387, E66/M61-F-99, E67/M50-F-150, E67/M62-F-214, E70/M54-F-133, E71/M47-F-550, E74/M61-F-385) and which nucleotide sequence confers resistance towards PMMoV pathotype 1.2.3.

As used herein, the term "Pepper mild mottle virus (PMMoV) pathotype 1.2.3" indicates a strain of Capsicum-infecting mild mottle virus which is able to overcome resistance conferred by the L3 allele. In literature, such strains are generally indicated with the term resistance-breaking strain of PMMoV. It is to be understood that the ICTV approved acronyms PMMoV and PMMV may both be used to indicate Pepper mild mottle virus. Synonyms for PMMoV that may be encountered in literature are: Samsun latent strain of tobacco mosaic virus (SL-TMV), pepper mosaic virus and Capsicum mosaic virus. Due to rapid developments in viral classification, some strains, notably the original Dutch strains (Tobias et al., 1982), that were initially classified as Pepper mild mottle virus (PMMoV; ICTV decimal code 71.0.1.0.007), are now classified as Paprika mild mottle virus (PaMMV; ICTV decimal code 71.0.1.0.006). The term "Pepper mild mottle virus (PMMoV) pathotype 1.2.3" as used herein therefore also includes PaMMV strains able to overcome resistance conferred by the L3 allele in pepper plants. In general, examples of viruses indicated by the term "Pepper mild mottle virus (PMMoV) pathotype 1.2.3" as used herein, include, but are not limited to, the following strains: isolate P14 of TMV (Boukema, 1982; Tobias et al., 1982; Rast, 1988); the Italian strains indicated by PMMoV-I (Wetter et al., 1984; Rodriguez-Cerezo et al., 1989; Velasco et al., 2002; Berzal-Herranz et al., 1995; Garcia-Luque et al., 1993); the Spanish strains indicated by PMMoV-S (Tenllado et al., 1997; Velasco et al., 2002; Tenllado et al., 1996; Berzal-Herranz et al., 1995; Garcia-Luque et al., 1993; Alonso et al., 1991; Avila-Rincon et al., 1989; Rodriguez-Cerezo et al., 1989.); the Japanese strains indicated by PMMoV-J and PMMoV-Ij (Tsuda et al., 1998; Hagiwara et al., 2002; Kirita et al., 1997); the Korean strains indicated by PMMV-k (Lim et al., 1997); and PaMMV (Garcia-Luque et al., 1993; Ruiz del Pino et al., 2003; Gilardi et al., 2004). Authoritative references for the description of Pepper mild mottle virus and Paprika mild mottle virus are i.a. Brunt, A. A., Crabtree, K., Dallwitz, M. J., Gibbs, A. J., Watson, L. and Zurcher, E. J. (eds.) (1996 onwards) "Plant Viruses Online: Descriptions and Lists from the VIDE Database," Version: 16 Jan. 1997; and The Universal Virus Database of the International Committee on Taxonomy of Viruses (Worldwide Website: ncbi.nlm.nih.gov/ICTVdb/index.htm).

A "truncated allele" is defined herein as an allele that is smaller in size, based on genetic distance, than the complete allele. The size reduction may for instance be shown by the absence of at least one linked marker and/or the absence of a distinguishable phenotype, in the present case the SNFD phenotype.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) in stead of "allele", however, in those instances, the term "allele" should be understood to comprise the term "haplotype". Alleles are considered identical when they express a similar phenotype. Differences in sequence are possible but not important as long as they do not influence phenotype.

A "genomic region" is defined herein as a nucleotide sequence, preferably a DNA sequence, that may comprise sequences with various genomic functions such as genes and regulatory elements regions. A genomic region may be a nucleotide construct and may be comprised in a vector. Alternatively, a genomic region may be transferred from one plant to another by chromosomal recombination after crossing said plants. A genomic region may in principle comprise genetic material originating from one or more species.

A "gene" is defined herein as a hereditary unit consisting of a sequence of DNA that occupies a specific location on a chromosome and that contains the genetic instruction for a particular characteristics or trait in an organism.

A "locus" is defined herein as the position on a genetic map that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes. Homozygosity is defined as absence of segregation after selfing of an individual plant or, if crossed to susceptible, absence of segregation in F1.

As used herein, the term "hybrid" means any offspring of a cross between two genetically unlike individuals (Rieger et al., 1968).

As used herein, the term "inbred" means a substantially homozygous individual or line.

In this application a "recombination event" is understood to mean a (meiotic) crossing-over.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

"Genetic engineering", "transformation" and "genetic modification" are all used herein as synonyms for the transfer of any kind of genetic information into the DNA of the target plant, usually but not exclusively the chromosomal DNA or genome, of another organism. Genetic engineering is one method of stably integrating heterologous genetic material in the genome of a recipient plant and may include a process comprises transforming cells or tissue of a plants with a DNA recombinant containing a heterologous DNA including a foreign nucleotide sequence encoding a gene or allelic variant thereof as well as the regulatory elements selected among those which are capable of causing the stable integration of heterologous DNA in plant cells or tissue and of enabling the expression of foreign nucleotide sequences in plant cells or plant tissue.

As used herein, the term "molecular marker" means a marker obtainable by using any technique such as a restriction fragment length polymorphism (RFLP) marker, amplified fragment length polymorphism (AFLP) marker, single nucleotide polymorphism (SNP) marker, microsatellite marker, a sequence characterized amplified repeats (SCAR) marker or an isozyme marker or combinations of the markers described herein which defines a specific genetic and chromosomal location and detect a polymorphism between two alleles. The markers of Group 1, 2, 3 and 1/3 as provided herein represent markers (in particular AFLP markers) consisting of a double stranded or single stranded nucleotide sequence obtained by performing a nucleic acid amplification reaction using *Capsicum* genomic DNA as a template and using the primer sequences indicated in FIG. 3 as first and second primer of a pair of amplification primers to provide a double stranded or single stranded nucleotide sequence consisting of a *Capsicum*-specific nucleotide sequence and/or its complement flanked on either side by said primer sequences and/or their complements. The term *Capsicum*-specific nucleotide sequence is used herein to indicate the sequence as obtained when using genomic DNA of *C. chacoense* accession PI 260429 as the template DNA and sequences having a sequence similarity thereto of at least 90%, preferable 95%, more preferably 97%, even more preferably more than 98%.

As used herein, the term "Restriction Fragment Length Polymorphism" or "RFLP" means a variation between individuals in DNA fragment sizes cut by specific restriction enzymes. Polymorphic sequences that result in RFLPs are used as markers on genetic linkage maps.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "pepper" or "*Capsicum*" means any species, variety, cultivar, or population of the *Capsicum* genus.

The present invention in one aspect provides a plant of the *Capsicum* genus that exhibits resistance to pepper mild mottle virus (PMMoV) pathotype 1.2.3. A plant of the *Capsicum* genus according to the present invention may be any species of the genus *Capsicum*, including, but not limited to *C. annuum, C. baccatum, C. cardenasei, C. chacoense, C. chinense, C. eximium, C. frutescens, C. microcarpum, C. minimum, C. pendulum, C. praetermissum* and *C. pubescens*. Preferably, a plant of the invention is a white flowering *Capsicum* species, preferably a *C. annuum, C. frutescens, C. chinense*, or *C. chacoense* plant, more preferably a *C. annuum, C. frutescens* or *C. chinense* plant, still more preferably a *C. annuum* or *C. frutescens* plant, most preferably *C. annuum*. In an even more preferred embodiment, the invention provides *C. annuum* plants having agronomically or commercially desirable characteristics.

As used herein, the term "*C. annuum*" means a pepper plant of the *Capsicum* genus, the genome of which plant comprises a *C. annuum* genome as a genetic background. Such a plant will essentially have a *C. annuum* genome, wherein as a result of recombination, transformation or any other process, DNA of other species has been integrated. The skilled person will understand that breeding between two plant species will result in plants that have characteristics and genetic material of both parents, thus obscuring the demarcation line between species. Such plants are all termed *C. annuum* plants herein.

The Tobamovirus Pepper mild mottle virus (PMMoV) was first reported in *C. annuum* in South Carolina, U.S.A. in 1952 (McKinney, 1952). Symptoms include mild chlorosis and stunting, especially if plants are infected when young. Fruits can be small, malformed, mottled and may have necrotic depressions, thus rendering them unmarketable. PMMoV is transmitted by close contact between plants, by virions on the surface of seeds, and by grafting. The virus has been reported in many countries (Argentina, Australia, Canada, Denmark, France, Hungary, Iceland, Italy, Japan, Korea, the Netherlands, Spain, the UK, and the USA). Control of the disease is best achieved by the use of resistant cultivars. New strains have been reported which reportedly are capable of overcoming resistance conferred by L4 alleles. (Antignus et al., 2000).

The resistance to Pepper mild mottle virus (PMMoV) pathotype 1.2.3 in plants of the invention is due to the presence of the L4 resistance allele in the genome of the plant. The L4 resistance allele present in the genome of the plant of the invention that confers the resistance to PMMoV pathotype 1.2.3, may originate form any source. According to a preferred embodiment of the present invention the L4 resistance allele originates from *C. chacoense*, more preferably from accessions PI 260429 and SA 185 (Boukema, 1983).

Plants of the invention are capable of transmitting PMMoV resistance to progeny and may be heterozygous for the L4 resistance allele, but are preferably homozygous for the L4 resistance allele. Plants of the present invention that are homozygous for the L4 resistance allele do not show reduced fertility and/or do not show dwarf growth.

When plants do not exhibit reduced fertility and/or dwarf growth, it is inferred that enough of the genetic information causing the SNFD phenotype is missing, or that this genetic information is sufficiently deactivated. The absence of the genetic information responsible for the SNFD phenotype is at least to such an extent that the SNFD phenotype is not expressed.

The present inventors have determined the presence of various genetic markers in the vicinity of the L4 allele by AFLP and have found that, based on recombination between markers or between a marker and L4-allele, these markers can be divided into distinct groups (see Table 1 in Examples). The position of the different groups linked to the L4-locus is shown in FIG. 1. Group 1 markers are thought to be in closest vicinity to the L4-allele itself as so far no recombination was observed between markers and resistant scores in a PMMoV pathotype 1.2.3. bioassay, indicating presence of the L4-allele. Group 2 and 3 markers are flanking the Group 1 markers on either side. A fourth group consists of markers positioned in the region spanning both Group 1 and 3. This group of markers is herein referred to as Group 1/3 markers.

The markers present in Group 1/3 are distinct in that so far each of these markers cannot be placed within Group 1 or Group 3 as no recombination has been observed between given marker and Group 1 markers, nor between given marker and Group 3 markers. As recombination is observed between Group 1/3 markers and Group 2 markers, markers from these 2 groups clearly differ in their genetic position and the actual position of these markers is either Group 1 or Group 3.

Thus far, no recombination was observed within each of the groups.

Orientation of the map of FIG. 1 towards the remainder of the chromosome is such that Group 2 markers are positioned centromeric and Group 3 markers are positioned telomeric (towards the end) on chromosome 11 south. I.e. the main portion of the allele is positioned below marker TG036 on chromosome 11 (Chr. P11 (brun)) for the segregating population PY as displayed in the intraspecific consensus linkage map of pepper as published in FIG. 1 of Lefebvre et al., 2002, to which figure explicit reference is made.

It was found that in plants that were resistant and homozygous for the L4 allele and that missed any of the markers of either Group 2, Group 3 or Group 1/3, and specifically Group 2, exhibited no SNFD phenotype. Thus, certain genomic regions that are normally linked to the L4 allele may be replaced with homologue DNA of other genotypes without affecting the resistance, yet strongly affecting the growth and fertility, as well as the behaviour of the inheritance of the resistance trait into offspring plants.

The plants without SNFD phenotype can for instance be obtained by means of conventional hybridization (plant crossing) techniques. A condition is however that the correct selection criterion is used. According to the invention a suitable selection criterion has now been defined, namely the complete or partial absence or inactivity of a piece of genetic information from the vicinity of the L4 resistance allele. According to the invention it is not relevant how much of the genetic information surrounding the resistance allele is absent from or is repressed in a recombinant or in which manner the gene(s) conferring the SNFD phenotype is or are deactivated, as long as the SNFD phenotype is absent from the plant and its progeny.

In order to find plants in which recombination has taken place between the L4 allele and genes causing the SNFD phenotype, segregating populations, or progeny of such populations, are in practice screened for plants having a recombinant phenotype, i.e. homozygous resistance to PMMoV P1.2.3 in combination with a non-SNFD phenotype.

Although it is possible to find suitable recombinants in this manner, there are a number of reasons why finding agronomically valuable recombinants can be complicated. As said before, homozygotes show the SNFD phenotype. However, it was found that if such homozygotes were crossed with a susceptible plant (i.e. containing no L4 allele) the $F_1$ showed resistance and no SNFD. This appeared to be due to the fact that the L4 resistance allele is dominant, while the genes responsible for the SNFD phenotype are recessive.

Progeny of a plant with a single copy of the *C. chacoense* chromosome fragment will thus combine resistance with a normal (non-SNFD) phenotype. However, their $F_1$ offspring will segregate for the resistance phenotype and such plants cannot be used commercially because commercial *Capsicum* varieties must comply with strict requirements of genetic uniformity in order to be brought into circulation.

Despite the above described difficulties which may occur, it will be apparent that the selection of the desired plants in which the genetic information for the SNFD phenotype is absent is very much possible in a conventional manner. This manner of selection does however require a relatively large segregating population or a large number of hybridizations for identification.

It may therefore be more efficient to make use of molecular biological tools in the selection of suitable plants. A useful technique is the AFLP technique, as described by Vos et al., 1995.

When applied to the present invention this technique is based on mapping DNA markers, which are genetically linked to the L4 allele, whereafter it can be determined in relatively simple manner whether a recombination event has occurred in the vicinity of the L4 allele in a progeny of a hybridization experiment. The efficiency of the selection of plants combining homozygosity for the L4 allele with absence of the SNFD phenotype can be significantly increased by using molecular markers. When a L4-linked marker is missing, a crossing-over between the L4 allele and that marker has (therefore) taken place. By choosing markers at various genetic distances from the allele, position of the recombination can be defined so it can be determined whether much or little has disappeared from the vicinity of the allele. Progeny wherein one or more of the linked markers is absent are therefore lacking at least a piece of the undesired vicinity of the allele and therefore have a more than average chance that a chromosome with the L4 allele is present, wherein the genetic information resulting in the SNFD phenotype is absent.

Mapping of genetic markers in the vicinity of a allele is a procedure which can be performed quite easily by the average person skilled molecular-biological techniques which techniques are for instance described in Lefebvre and Chevre, 1995; Michelmore, 1995; Winter and Kahl, 1995. General information concerning AFLP technology can be found in Vos et al. (supra).

Plants according to the invention in the embodiment wherein the L4 resistance allele is present in homozygous condition and that do not express the SNFD phenotype can suitably be used to transfer PMMoV P1.2.3 resistance into other agronomically valuable *Capsicum* types. Hybrid pepper plants can thus be produced by crossing a homozygous plant, preferably an inbred line, with another pepper plant. The other pepper plant may or may not be resistant to PMMoV P1.2.3, is preferably homozygous and is even more preferably an inbred line.

Plants according to the invention in the embodiment wherein the L4 resistance allele is present in homozygous condition and that do not express the SNFD phenotype, can also be used to fix the PMMoV P1.2.3 resistance into other agronomically valuable *Capsicum* types. This may for instance take place by means of standard backcrossing procedures (see e.g. Briggs and Knowles, 1967), followed by self-pollination of the plants for at least two generations and the selection of lines which are homozygous for the resistance allele and that do not express the SNFD phenotype.

In particular steps of the selection program, cross-pollinations are used. However, cross-pollination of self-pollinating plants requires that self fertilization is prevented in the plant which is used as the female parent. This can be achieved by manually removing the male parts of the reproductive organs. This can be effected by physical removal thereof or by means of chemical agents and/or the use of water on the flowers. All these methods of removing or rendering dysfunctional the male parts of the reproductive organs are well known in the art. Progeny of a hybridization can be obtained by causing the female parent of the hybridization to produce seed, collecting the $F_1$ or backcross seed and sowing it to obtain new plants. $F_1$ plants can be self-pollinated to produce the $F_2$ generation or backcrossed with the recurrent parent of a backcross scheme. Backcrossed plants can be further crossed with the (recurrent) parent to improve the agronomic value of the plants in a subsequent generation or can be self-pollinated to produce plants which are homozygous for the L4 allele and that do not express the SNFD phenotype.

The present invention is illustrated in this application with reference to *Capsicum annuum*. It will be apparent to the skilled person that the principles of the invention are likewise applicable to other species of the genus *Capsicum*, and more generally to plants of the family Solanaceae wherein the L4 allele can be introduced to confer PMMoV resistance. In principle, the various aspects of the present invention may relate to all plants that can be affected by PMMoV, and the principles of the invention are likewise applicable to any plant species within the host range of PMMoV. In this context, special reference is made to the host range for PMMoV as described in the website publication that is officially cited as "Brunt, A. A., Crabtree, K., Dallwitz, M. J., Gibbs, A. J., Watson, L. and Zurcher, E. J. (eds.) (1996 onwards). '*Plant Viruses Online Descriptions and Lists from the VIDE Database*. Version: 20 Aug. 1996.' (Worldwide Website: biology-.anu.edu.au/Groups/MES/vide/"), but which may i.a. be found at the Worldwide Website: image.fs.uidaho.edu/vide/ refs.htm. In this context, Dallwitz, 1980 and Dallwitz et al., 1993 should also be cited. Reference to *C. annuum* should not therefore be interpreted as a limitation of the invention.

In addition to the *Capsicum* plants themselves, and the parts thereof suitable for consumption, such as the fruits, the invention comprises parts of the plant suitable for propagation. As described above, the invention is not limited to plant parts of *Capsicum* plants, but relates to parts of any plant within the host range of PMMoV. Examples of parts suitable for propagation are organ tissues, such as seeds, leaves, stems, roots, shoots and the like, protoplasts, somatic embryos, anthers, petioles, cells in culture and the like. The plants according to the invention can be cultivated or propagated in the conventional manner but also by means of tissue culture techniques from plant parts.

A method of the invention for producing a plant of the *Capsicum* genus that exhibits resistance to PMMoV pathotype 1.2.3 comprises the step of providing a suitable recipient plant of the *Capsicum* genus which is susceptible to PMMoV pathotype 1.2.3.

A method of the invention for producing a plant of the *Capsicum* genus that exhibits resistance to PMMoV pathotype 1.2.3 further comprises the step of introducing into said recipient plant an L4 resistance allele, for instance from a donor plant, which L4 resistance allele confers resistance to PMMoV pathotype 1.2.3 to said recipient plant.

A method of the invention for producing a plant of the *Capsicum* genus that exhibits resistance to PMMoV pathotype 1.2.3 may further comprise the step of producing a segregating population from said resistant plant.

A method of the invention for producing a plant of the *Capsicum* genus that exhibits resistance to PMMoV pathotype 1.2.3 may further comprise the step of producing a progeny of substantially each plant of said segregating population. A progeny or offspring may be produced by allowing said plant to produce seed, for instance by crossing or selfing said plant, and growing said seed into a new plant. Alternatively a progeny may be obtained by using other suitable techniques. Such alternatives are quite common in the area of plant breeding.

A method of the invention for producing a plant of the *Capsicum* genus that exhibits resistance to PMMoV pathotype 1.2.3 comprises the step of selecting from at least one of said progenies a plant in the genome of which the L4 resistance allele is present and in which genome the genetic information responsible for the SNFD phenotype is absent at least to such an extent that the SNFD phenotype is not expressed.

The presence of the L4 resistance allele in the genome of the plants of the present invention may be the result of any cause, natural or artificial, and may for instance be the result of introgression, genetic engineering (transformation) or protoplast fusion.

The introgression of one or more genes encoding for L4 resistance from a donor plant into a recipient plant that is non-resistant or possesses low levels of resistance to PMMoV can be accomplished using techniques known in the art. For example, one or more genes encoding for PMMoV resistance, i.e., the L4 allele, can be introgressed into a recipient pepper plant that is non-resistant or a plant that has low levels of resistance to PMMoV using traditional breeding techniques, optionally in combination with molecular screening methods, for instance by using markers.

Traditional breeding techniques can suitably be used to introgress one or more genes encoding for PMMoV resistance from a donor plant into a recipient plant that is non-resistant or has a low level of resistance to PMMoV. These methods involve traditional crossing of species, varieties or cultivars, provided that such species, varieties or cultivars can be crossed with one another. A bridge species may be used when the projected donor and recipient species can only be crossed with one another to a limited extent.

In one traditional breeding method, which is referred to as pedigree breeding, a first pepper plant that exhibits resistance to PMMoV and contains the L4 allele encoding for PMMoV resistance is crossed with a second pepper plant that is non-resistant to PMMoV or possesses low levels of resistance to PMMoV and that exhibits agronomically or commercially desirable characteristics, such as, but not limited to, disease resistance, insect resistance, valuable fruit characteristics, etc. The resulting plant population (i.e. the $F_1$) is then allowed to self-pollinate and set seeds ($F_2$ seeds).

The $F_2$ plants grown from the $F_2$ seeds are then screened for resistance to PMMoV. The population can be screened in a number of different ways. First, the population can be screened using a traditional pathology disease screen also termed a resistance bioassay herein. Such bioassays for PMMoV are known in the art. Specifically, the individual plants or parts thereof can be challenged in an incubator or greenhouse with PMMoV and the resulting resistant or susceptible phenotypes of each plant scored. By way of example, and not of limitation, plants can be screened in a greenhouse as follows: Pepper plants can be grown from $F_2$ seeds in a greenhouse under growing conditions generally applied for their cultivation and known to the skilled person, for instance at a temperature of 22° C. during the day and 20° C. during the night, under normal summer-light conditions. The $F_2$ plants may for instance be grown in trays that also contain control plants, such as one or more resistant plants and one or more susceptible plants. As an inoculum infected leaves may be used, which may be stored frozen. An inoculum comprising the test virus may be prepared by grinding the infected leaves with water (e.g. 1 g of frozen leaf in 100 ml of water) and adding carborundum (silicon carbide). Inoculation of the test plant may for instance be performed by rubbing the inoculum onto an area of the surface (for instance minimal 3.5×2 cm) of the first true leaf of the plant using a sponge. After a first observation the plants that are visibly susceptible (visible symptoms are systemic mosaic) may be removed. During a second observation a week later, the number of susceptible an resistant plants may be counted. For a leaf-test, the leaves (4-5 cm from the top of the plant) may be placed in a tray containing wet filter paper and leaves are placed on top of the filter paper. Susceptible and resistant controls are added to the tray and the tray may be wrapped in plastic and incubated at 20° C. at a light regime of 16 hours/day. Inoculation may occur as described above with a sponge and evaluation occurs after 6-8 days.

Alternatively traditional breeding methods may be performed in combination with molecular screening methods. Such methods are commonly referred to as marker-assisted selection or marker-assisted breeding and involve the use of one or more of the molecular markers to identify those offspring plants that contain one or more of the genes that encode for the desired trait (i.c. the L4 allele, or the truncated form thereof). The genetic constitution of the genome predicts the plant's phenotype and lengthy bioassays become unnecessary. Marker assisted selection may also be used to confirm the results obtained from the bioassay screen. F2 hybrid plants that exhibit a PMMoV resistant phenotype contain the desired genes encoding for PMMoV resistance, and those that additionally possess commercially desirable characteristics are then selected and selfed for a number of generations in order to allow for the pepper plant to become increasingly inbred. The result of such breeding and selection is the production of lines that are genetically homogenous for the genes associated with PMMoV resistance as well as other genes associated with traits of commercial interest.

The present invention now provides a method of producing a plant of the *Capsicum* genus that exhibits resistance to PMMoV pathotype 1.2.3, comprising the steps of:

a) providing a first plant of the *Capsicum* genus that is susceptible to PMMoV pathotype 1.2.3 or a part thereof;
b) providing a second plant of the *Capsicum* genus that exhibits resistance to PMMoV pathotype 1.2.3 due to the presence of the L4 resistance allele in the genome of said plant;
c) crossing said first and second plant to produce progeny plants that exhibit resistance to PMMoV pathotype 1.2.3, and
d) further screening the genome of said resistant progeny plants for the presence of a truncated L4 resistance allele wherein said allele comprises genetic information that confers resistance to PMMoV pathotype 1.2.3 to said progeny plant, and wherein genetic information that confers the SNFD phenotype is absent from said allele at least to such an extent that the SNFD phenotype is not expressed.

In preferred embodiments of this method, the screening in step d) is performed by assessing the absence of at least one marker of the L4 resistance allele selected from the group consisting of Group 2 markers, Group 1/3 markers and Group 3 markers as shown in FIG. 3, preferably Group 2 markers as shown in FIG. 3.

According to a method of the present invention, the commercially desirable characteristics selected include the absence of the SNFD phenotype, meaning that the plants are non-segregating, fertile and exhibit normal growth, when compared to commercial *Capsicum* varieties that are non resistant to PMMoV pathotype 1.2.3. These characteristics may be identified in a plant by any suitable method. For instance, normal growth characteristics may be identified by visual inspection of the growth performance wherein the absence of dwarf growth indicates a normal growth. Fertility may be assessed by visual inspection of the amount of seed and/or pollen. A non-segregating phenotype may be assessed by evaluation of test results of resistance screen on F1 seeds of the cross (resistant×susceptible) as described above.

Alternatively, the absence of the SNFD phenotype may be assessed by screening the plants for the absence of specific markers. In one particularly preferred embodiment of plants and methods of the invention, one or more of the markers of Group 2 as described herein are absent. A method of the invention for producing a plant of the *Capsicum* genus that exhibits resistance to PMMoV pathotype 1.2.3 thus in one preferred embodiment comprises the step of selecting, from at least one of the progenies of a segregating population from a resistant plant, a plant in the genome of which one or more, preferably all, markers of Group 1, as described herein, are present, and in the genome of which one or more markers of Group 2, as described herein, are absent.

In another embodiment of a plant of the invention, one or more of the markers of Group 3 as described herein are absent. In still another embodiment of a plant of the invention, one or more of the markers of Group 1/3 as described herein are absent. In this context the absence of one or more markers of Group 1/3 should be understood as relating to those markers only which are not located in the genomic region that is responsible for the resistance to PMMoV pathotype 1.2.3, since the absence of such information would not result in a plant that exhibits resistance to PMMoV pathotype 1.2.3 due to the presence of the L4 resistance allele in the genome of that plant. Therefore the absence of one or more markers of Group 1/3 relates preferably only to those markers located in the region corresponding to that of the Group 3 markers, preferably not to that of Group 1 markers. In a most preferred embodiment, the L4 allele is truncated such that one or more Group 2 markers are absent. In this case, the truncation is centromeric, whereas in the case of a Group 3 marker truncation the truncation is telomeric. In another most preferred embodiment, the truncation is such that the TG036 (Lefebvre et al., 2002; Ben-Chaim et al, 2001) marker (a member of Group 2 markers) is absent.

The absence of the SNFD phenotype in plants provided with the L4 allele may thus be realized by introducing into plants a truncated form of the *C. chacoense* introgression comprising the L4 allele, herein also termed a truncated L4 allele. The degree of truncation can easily be determined by the skilled person. For instance, a suitable level of truncation can be achieved by the partial or complete removal, either by transgenic procedures or by a process of recombination and selection, of any one of those regions of the introgression that comprise the Group 2, Group 3, and/or Group 1/3 markers, provided that when regions comprising Group 1/3 markers are removed only those parts may be removed that do not harbour the information that is responsible for the resistance to PMMoV pathotype 1.2.3. Preferably said truncation involves the partial or complete removal of regions of the *C. chacoense* introgression comprising the L4 allele that comprise the Group 2 markers. Thus, the removal of a region comprising one or more Group 2 markers, either by transgenic procedures or by a process of recombination and selection, will result in a plant that does no longer express the SNFD phenotype. Most preferably this truncation results in the removal of the TG036 marker (Lefebvre et al., 2002; Ben-Chaim et al, 2001).

The level of truncation may also be defined as a genetic distance. Genetic distance is measured by frequency of crossing-over between loci on the same chromosome. The farther apart two loci are, the more likely that a crossover will occur between them. Conversely, if two loci are close together, a crossover is less likely to occur between them. The loci may be indicated by the markers of the various marker groups defined herein. As a rule, one centimorgan (cM) is equal to 1% recombination between loci (markers). The level of truncation that results in the absence of one or more markers of Group 2, Group 3 and/or Group 1/3, may suitably be 0.001-10 cM, more preferably 0.01-10 cM. Alternatively the genetic distance between a marker that indicates the presence of the introgression (e.g. one or more markers of Group 1) and a marker that is truncated may suitably be 0.001-10 cM, more preferably 0.01-10 cM.

A new and superior PMMoV resistant inbred pepper plant line can also be developed by using the technique of recurrent selection and backcrossing. In this method, L4 resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has a low level of resistance to PMMoV and possesses commercially desirable characteristics, such as, but not limited to disease resistance, insect resistance, valuable fruit characteristics, etc, and wherein the SNFD phenotype is absent. Backcrossing procedures are widely applied for crossing genes from a "donor parent" into a genetic background with a high agronomic value. In general the introgression of a dominant gene into an agronomically acceptable phenotype can be achieved by 3-5 backcrosses, followed by for instance 2-3 self pollinations, where in all steps selection to agronomic value is executed. The non-recurrent parent exhibits PMMoV resistance and contains the L4 resistance allele. The non-recurrent parent or donor plant can be any plant variety or inbred line that is cross-fertile with the recurrent parent or target recipient plant. The progeny resulting from a cross between the recurrent parent and non-recurrent parent are backcrossed to the recurrent parent. The resulting plant population is then screened. The population can be screened in a number of different ways. First, the population can be screened using a traditional pathology screen as described previously herein.

Second, marker-assisted selection can be performed using one or more of the hereinbefore described molecular markers to identify those progenies that contain the L4 resistance allele and from which one or more of the markers associated with the SNFD phenotype are absent. Alternatively, marker-assisted selection can be used to confirm the results obtained from the resistance bioassay screen.

Once the appropriate selections are made, the process is repeated. The process of backcrossing to the recurrent parent and selecting for PMMoV resistance and absence of the SNFD phenotype (or markers associated therewith) is repeated for approximately five or more generations. The progeny resulting from this process are heterozygous for the L4 allele. The last backcross generation is then selfed in order to provide for homozygous pure breeding progeny comprising L4 allele-conferred PMMoV resistance and lacking the SNFD phenotype.

The PMMoV resistant inbred pepper lines described herein that are homozygous for the L4 allele and that do not express the SNFD phenotype can be used in additional crossings to create PMMoV resistant hybrid plants. For example, a first PMMoV resistant inbred pepper plant can be crossed with a second inbred pepper plant possessing commercially desirable traits such as, but not limited to, disease resistance, insect resistance, desirable fruit characteristics, etc. This second inbred pepper line may or may not be resistant to PMMoV.

Selection procedures used in aspects of the present invention may involve the provision of a nucleic acid sample, preferably DNA, from plants, such as may be obtained by using nucleic acid isolation procedures well known in the art, and testing the sequence of said nucleic acid for the presence or absence of markers. The markers as defined herein are AFLP markers that may be detected by performing the AFLP reaction that led to their definition or, alternatively, by performing an amplification reaction, such as PCR, with one or more sets of marker-specific primers which, under conditions wherein said primers can anneal to their specific template, are capable of producing a specific amplification product. The presence of a specific amplification product then indicates the presence of the marker in the template sequence, whereas the absence of an amplification product indicates the absence of the marker. In order to confirm the presence of the L4 introgression (the L4 allele) one or more, preferably all, markers of Group 1, most preferably marker E58/M50-F-580 and/or marker E54/M55-F-101, as described herein, are detected in the nucleic acid sample. In order to confirm the presence of a properly truncated allele, preferably one or more markers of Group 2, as described herein, are absent. Some of the AFLP markers may also be converted into sequence tagged site markers, which allows a fast and convenient screening of progeny of crosses (Werner et al., 2001).

Alternatively, a method of screening for the presence or absence of L4 markers in the genome of a plant a sample may comprise contacting a nucleic acid sample from a plant with a probe which binds selectively to a target polynucleotide sequence on a chromosomal region comprising one or more marker sequences, wherein the probe is contacted with the sample under conditions in which the probe binds selectively with the target polynucleotide sequence to form a stable hybridization complex; and detecting the presence or absence of a hybridization complex, thereby screening for the presence or absence of said markers in the plant.

The marker-assisted selection used in the hereinbefore described methods can, for instance, be made step-wise, whereby the presence of the L4 allele and the absence of the SNFD phenotype is selected in more than one generation. Marker-assisted selection for L4 allele-conferred resistance may be done before, in conjunction with, or after testing and selection for other commercially desirable traits such as disease resistance, insect resistance, desirable fruit characteristics, etc. Likewise the order in which the PMMoV resistance or absence of SNFD phenotype is assessed is not particularly limiting. It should be understood that the (preferably marker-assisted) exclusion of plants comprising genetic information conferring the SNFD phenotype may be performed before the (preferably marker-assisted) selection of PMMoV resistant plants, or even simultaneously.

A source of material from which the L4 allele can be isolated from its naturally surrounding environment, thus obtaining only the genetic information conferring the L4 resistance and not the genetic information conferring the SNFD phenotype, is for instance from a plant of *C. chacoense* accessions PI 260429 or SA 185 (Boukema, 1983). Such accessions are for instance available from Plant Genetic Resources (PGR) cluster of the Centre for Genetic Resources, the Netherlands (CGN), Wageningen, The Netherlands.

An isolated nucleic acid sequence comprising a truncated L4 resistance allele according to the invention may for instance be produced by isolating DNA from a plant that is resistant to PMMoV pathotype 1.2.3 and isolating from said DNA an L4 resistance allele. Such an isolation may for instance be achieved by amplifying the genetic region comprising the PMMoV resistance-conferring part of said L4 allele, for instance by using suitable forward and reverse primers. Suitable primers are for instance those used for the definition of markers of Group 2, together with markers used for the definition of markers of Group 3. The size of the amplification fragment can be reduced by using or developing other primers that anneal on locations of the *C. chacoense* genome that are less far apart, for instance closer to the position of the markers of Group 1. In this way it can be achieved that genetic information that confers the SNFD phenotype is absent from the L4 allele. The skilled person is aware of the various regulatory elements that must be present in such a nucleic acid for it to be expressed in a plant of the *Capsicum* genus thereby conferring resistance to PMMoV pathotype 1.2.3 to said plant.

The L4 allele or the L4 gene may for instance also be isolated by providing a sample of genomic DNA from a *Capsicum* plant using standard DNA isolation methods well known in the art. It is required in order retrieve large DNA fragments that the quality of the isolate is relatively high, that is, that severe degradation of the genomic DNA is essentially avoided. Generally, DNA of sufficient length may be obtained if isolation techniques for obtaining high molecular weight (HMW) DNA preparations are employed. HMW DNA is DNA that is obtained under protection from physical shearing during preparation. The preparation of HMW DNA from *Capsicum* plant tissue may for instance involve isolating protoplasts using cell wall hydrolysis and embedding the protoplasts in agarose. An alternative method is preparing HMW DNA from plant nuclei. The isolation of megabase DNA has been successfully carried out for a large number of plant species and such methods are now commonly applied to provide megabase-size DNA suitable for constructing large insert DNA libraries in bacterial artificial chromosome (BAC) and yeast artificial chromosome (YAC) cloning vectors. Once the genomic DNA is isolated, it may be treated for instance by using the restriction enzymes, used in PCR amplification reactions or may be cloned or probed with any of the marker sequences provided herein.

The present invention further contemplates the insertion of such isolated and purified genes (or alleles) either into pepper or other plants using techniques known in the art in order to provide transgenic plants that exhibit resistance to PMMoV infection. Plant transformation involves the construction of an expression vector that will function in plant cells. In the present invention, such a vector comprises DNA comprising a gene that encodes for PMMoV resistance that is under control of or operatively linked to a regulatory element, such as a promoter. The expression vector may contain one or more such operably linked gene/regulatory element combinations, provided that at least one of the genes contained in the combinations encodes for PMMoV resistance. The vector(s) may be in the form of a plasmid, and can be used, alone or in combination with other plasmids, to provide transgenic plants that are resistant to PMMoV, using transformation methods known in the art, such as the *Agrobacterium* transformation system.

Expression vectors can include at least one genetic marker, operably linked to a regulatory element (such as a promoter) that allows transformed cells containing the marker to be either recovered by negative selection (by inhibiting the growth of cells that do not contain the selectable marker gene), or by positive selection (by screening for the product encoded by the genetic marker). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (See e.g. Kado, 1991). Methods of introducing expression vectors into plant tissue include the direct infection or co-cultivation of plant cells with *Agrobacterium tumefaciens*, Horsch et al., 1985). Descriptions of *Agrobacterium* vectors systems and methods for *Agrobacterium*-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips et al., 1988. A proper reference handbook for molecular cloning techniques and suitable expression vectors is Sambrook, J., E. F. Fritsch, and T. Maniatis. Molecular Cloning: a Laboratory Manual (3rd. edition). Cold Spring Harbor Laboratory Press, Plainview, N.Y., 2000.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (See, Zhang et al., 1991). Alternatively, liposome or spheroplast fusion has been used to introduce expression vectors into plants (See e.g. Deshayes et al., 1985 and Christou et al., 1987). Direct uptake of DNA into protoplasts using $CaCl_2$ precipitation, polyvinyl alcohol or poly-L-ornithine has also been reported (See e.g., Hain et al., 1985 and Draper et al., 1982). Electroporation of protoplasts and whole cells and tissues has also been described (D'Halluin et al., 1992 and Laursen et al., 1994).

Following transformation of pepper target tissues, expression of the above described selectable marker genes allows for preferential selection of transformed cells, tissues and/or plants, using regeneration and selection methods now well known in the art.

The foregoing methods for transformation could be used for producing transgenic pepper plants or other plant species, such as, but not limited to Solanaceae species. As stated before, the various aspects of the present invention may in principle relate to all plants that can be affected by PMMoV, and transgenic plants according to the invention may thus be produced in any plant species within the host range of PMMoV.

Such transgenic plants can then be crossed, with another (nontransformed or transformed) plant, in order to produce a transgenic hybrid of pepper or other plant species that is resistant to PMMoV infection. Alternatively, the foreign (heterologous) genes for PMMoV resistance in a transgenic pepper or other plant species that has been engineered to contain the foreign (heterologous or homozygous) gene(s) that encode(s) for PMMoV resistance using the transformation techniques described herein could be moved into another plant using traditional breeding techniques (such as backcrossing), that are well-known in the art. For example, and as previously discussed herein, backcrossing could be used to introgress PMMoV resistance from a transgenic PMMoV resistant inbred pepper or other plant line containing a foreign (heterologous) gene that encodes for PMMoV resistance and that does not contain the genetic information responsible for the SNFD phenotype to a non-resistant pepper plant or other crop that does not contain that gene, or from a transgenic hybrid PMMoV resistant pepper plant or other plant containing a foreign gene that encodes for PMMoV resistance into a line (s) that does not contain that gene.

In another embodiment, protoplast fusion can be used to create superior new PMMoV resistant plants. More specifically, a first protoplast can be obtained from a pepper plant or other plant line that exhibits resistance to infection by PMMoV and that does not contain the genetic information responsible for the SNFD phenotype. A second protoplast can be obtained from a second pepper or other plant variety that contains commercially desirable characteristics, such as, but not limited to disease resistance, insect resistance, valuable fruit characteristics, etc. The protoplasts are then fused using traditional protoplast fusion procedures which are known in the art. For example, the protoplast fusion can be accomplished by employing a polyethylene glycol (PEG) solution to facilitate the fusion of the membranes. Such somatic hybridization may be effected under the conditions disclosed by Sundberg et al., 1986, for the production of interspecific hybrids or modifications thereof. However, one skilled in the art would recognize that the protoplast fusion can be accomplished in other ways other than using polyethylene glycol (PEG). For example, the protoplasts can be fused by using electric field-induced fusion techniques as described by Koop and Spangenberg, 1989. Additionally, protoplast fusion can be accomplished with dextran and polyvinyl alcohol. Additional methods for protoplast fusion may be found in Gleba et al., 1984 and in Dodds and Roberts, 1995.

By way of example, and not of limitation, Examples of the present invention will now be given.

EXAMPLES

Two inbred parental lines, named male parent of Sylvia (inbred line of S&G variety "Cuby") and male parent of Manito (inbred line of S&G variety "Tasty") were produced. Both varieties Sylvia and Manito initially segregated for PMMoV resistance. By plant selection and test crossings it was possible to fix resistance in both varieties. However, it was noted that traits like non-stable male sterility/bad fertility and dwarf growth were present in the male parents of both varieties.

The PMMoV pathotype 1.2.3. that is used in these Examples is a virus isolate with similar characteristics as isolate P14 mentioned by Boukema, 1982. In the following Examples, the virus isolate used in the various experiments was received from PTG (Proefstation voor Tuinbouw onder Glas), now PPO, in Naaldwijk, The Netherlands, and was mechanically propagated.

Example 1

L4 Resistance Markers in Resistant and Susceptible Pepper Plants within the Same Variety A linkage map of the L4-locus was produced by Keygene (Wageningen, The Netherlands). The region where the L-locus was mapped was located on the telomere of chromosome 11-south (Lefebvre et al., 2002).

Markers around this locus could be divided in four groups. The position of the different groups linked to the L4 locus is shown in FIG. 1. Each group contains a number of markers, within each group no recombination was found. Orientation of the linkage map towards the remainder of the chromosome is unknown. The markers present within each group are shown in Table 1.

TABLE 1

Overview of markers within respective groups.

| Group 1 (L4 allele specific) | Group 1/3 | Group 3 | Group 2 |
|---|---|---|---|
| E39/M58-F-95 | E63/M61-F-501 | E60/M54-F-447 | E35/M49-F-90 |

TABLE 1-continued

Overview of markers within respective groups.

| Group 1 (L4 allele specific) | Group 1/3 | Group 3 | Group 2 |
|---|---|---|---|
| E54/M55-F-101 | E66/M43-F-387 |  | E39/M58-F-65 |
| E58/M60-F-255 | E66/M49-F-387 |  | E39/M51-F-380 |
| E58/M50-F-580 | E66/M61-F-99 |  | E58/M62-F-168 |
|  |  | E67/M50-F-150 | E66/M54-F-600 |
|  |  | E67/M62-F-214 | TG036 |
|  |  | E70/M54-F-133 |  |
|  |  | E71/M47-F-550 |  |
|  |  | E74/M61-F-385 |  |

From the segregating varieties Manito and Sylvia, $F_1$ plants as well as resistant parental lines were tested in a bioassay, quite similar as that described above. In total, a tray consisted of 35 test plants, including one susceptible control and one resistant control. The stem and leaf test bioassays were performed essentially as described above. The results of the bioassay are shown in Table 2.

TABLE 2

Results of bio-assay on varieties Sylvia and Manito and their resistant parental lines.

| Name | No. of resistant plants | No. of susceptible plants | Test no. in Marker test |
|---|---|---|---|
| Manito | 14 | 11 | 23-28 |
| Father of Manito | 20 | 0 | 29-33 |
| Sylvia | 19 | 11 | 34-39 |
| Father of Sylvia | 20 | 0 | 40-44 |

From the bioassay shown in Table 2, 3 resistant and 3 susceptible plants were randomly chosen from the $F_1$ plants of both segregating varieties Manito and Sylvia, as well as 5 plants were randomly chosen from their corresponding resistant male parents. Chosen plants were further analysed with 4 markers, listed in Table 1, linked to the L4 locus. Not all markers, listed in table 1, were identified at the time the test was performed. Of each variety, the three resistant and three susceptible plants were analysed by testing for the presence of the various markers. From the corresponding resistant parent, five plants were analysed. Results of the marker analysis are listed in table 3.

TABLE 3

Marker scores (dominant, see text) of selected plants from bioassay.

|  | Manito | | | | | | male parent of Manito | | | | | Sylvia | | | | | | male parent of Sylvia | | | | |
|---|---|---|---|---|---|---|---|---|---|---|---|---|---|---|---|---|---|---|---|---|---|---|
| Number | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| Phenotype | R | R | R | S | S | S | R | R | R | R | R | R | R | R | S | S | S | R | R | R | R | R |
| L4 markers (group) | | | | | | | | | | | | | | | | | | | | | | |
| E39/M58-F-95 (1) | + | + | + | − | − | − | + | + | + | + | + | + | + | + | − | − | − | + | + | + | + | + |
| E39/M58-F-65 (2) | + | + | + | − | − | − | + | + | + | + | + | + | + | + | − | − | − | + | + | + | + | + |
| E58/M50-F-580 (1) | + | + | + | − | − | − | + | + | + | + | + | + | + | + | − | − | − | + | + | + | + | + |
| E58/M60-F-255 (1) | + | + | + | − | − | − | + | + | + | + | + | + | + | + | − | − | − | + | + | + | + | + |

Numbers correspond to the test number in the Marker test; R, resistant; S, susceptible; +, present; −, absent.

As can be seen from Table 3, all markers linked to the L4 allele were present in $F_1$-plants that exhibited phenotypic resistance in the bioassay (R). In the susceptible plants (S) however, none of the L4 markers were present. The resistant male parents of Manito (Nos. 29-33) and Sylvia (Nos. 40-44) showed no segregation in the bioassay and all markers linked to the L4 allele were present in these plants. As markers were solely scored present or absent (dominant), it could not be concluded if the introgression segment was present homozygous or heterozygous. It was concluded that susceptibility in the $F_1$ is caused by absence of the L4 introgression. Additional testing revealed that maternal effects in the inheritance of L4 resistance were absent.

Example 2

Development of Non-Segregating Sylvia Variety

To develop a non-segregating variety Sylvia, individual plants of the resistant parental line (line 4578) were crossed to plants of the susceptible parent. The occurrence of segregation of L4 resistance was evaluated in the resulting individual $F_1$ populations. Results are listed in Table 4.

Line 6636 was obtained by selfing of plant no. 4578-8. Individual plants of line 6636 are listed more than once because these plants were used as male on different (but related) susceptible female lines.

None of the plants of line 4578 resulted in a completely resistant $F_1$. However, by selfing line 4578 (vide line 6636) it was possible to find lines that transferred the resistance gene for 100%. In 4 out of 10 cases, this resulted in a completely resistant $F_1$. The segregation of the $F_1$ derived from plant no. 6636-4 shows a pattern that is different from the other lines. As shown in Table 4, there is variation in the number of resistant plants in the segregating $F_1$ populations (2R/3S-3R/2S). Segregation is expected to be more reliable when the number of resistant and susceptible plants in segregating $F_1$ populations is combined. As the same source of resistance is used in all $F_1$ populations the cause of the non-stable (segregating) resistance is the same. Table 8 shows the compiled results of each of the three crossings mentioned in Table 4 (4578, 6636cross1 and 6636cross2; the two 6636 crosses are the result of two different susceptible parents being crossed with identical resistant plants.

TABLE 4

$F_1$ segregation of Sylvia, derived from individual plants.

| Plant no. of resistant parent | No. of resistant F1 plants | No. of susceptible F1 plants |
|---|---|---|
| 4578-1 | 1 | 4 |
| 4578-2 | 31 | 19 |
| 4578-3 | 20 | 30 |
| 4578-4 | 24 | 26 |
| 4578-5 | 30 | 20 |
| 4578-7 | 24 | 26 |
| 4578-8 | 27 | 23 |
| 4578-9 | 31 | 19 |
| 4578-10 | 26 | 24 |
| 6636-1 | 50 | 0 |
| 6636-2 | 19 | 21 |
| 6636-4 | 50 | 0 |
| 6636-5 | 31 | 19 |
| 6636-6 | 26 | 24 |
| 6636-6 | 27 | 23 |
| 6636-8 | 24 | 26 |
| 6636-9 | 33 | 0 |
| 6636-10 | 50 | 0 |

TABLE 4-continued $F_1$ segregation of Sylvia, derived from individual plants.

| Plant no. of resistant parent | No. of resistant F1 plants | No. of susceptible F1 plants |
|---|---|---|
| 6636-1 | 50 | 0 |
| 6636-2 | 29 | 21 |
| 6636-3 | 40 | 0 |
| 6636-5 | 34 | 16 |
| 6636-6 | 27 | 23 |
| 6636-7 | 24 | 26 |
| 6636-8 | 33 | 17 |
| 6636-9 | 50 | 0 |
| 6636-10 | 50 | 0 |
| 6636-1 | 50 | 0 |
| 6636-2 | 31 | 19 |
| 6636-3 | 50 | 0 |

Selfings of individual plants of line 6636, used for producing the $F_1$ populations in Table 4, were also tested for PMMoV resistance. All selfed lines showed complete resistance. Results are listed in table 5.

TABLE 5 results of selfings from parental lines

| Plant no. of resistant parent | No. of resistant plants | No. of susceptible plants |
|---|---|---|
| 6636-1 | 50 | 0 |
| 6636-2 | 50 | 0 |
| 6636-3 | 50 | 0 |
| 6636-4 | 50 | 0 |
| 6636-5 | 50 | 0 |
| 6636-6 | 50 | 0 |
| 6636-7 | 50 | 0 |
| 6636-8 | 50 | 0 |
| 6636-9 | 50 | 0 |
| 6636-10 | 50 | 0 |

From this experiment the unwanted characteristic of the L4 allele becomes clear as it can be concluded that selfing of individual plants that results in a non-segregating offspring confirms homozygosity, whereas crossing of individual resistant plants to susceptible plants results in a segregating $F_1$ offspring and confirms heterozygosity.

Example 3

Development of Non-Segregating Manito Variety

A similar approach as described in Example 2 was followed to develop a non-segregating Manito line. Plants of the resistant parental line were individually crossed with plants of the susceptible parent and the segregation in the individual $F_1$ populations was evaluated. Results are listed in Table 6. All plants that showed low fertility (SNFD phenotype) were removed before crossing, these plants are listed in Table 6 as "not tested". Low fertility was initially not observed in plant no. 0025-5 but appeared later to be present.

TABLE 6

F₁ segregation of Manito, derived from individual plants (first screening)

| Plant no. of resistant parent | No. of resistant F1 plants | No. of susceptible F1 plants |
|---|---|---|
| 0021-1 | 39 | 11 |
| 0021-2 | 34 | 16 |
| 0021-3 | 34 | 16 |
| 0021-4 | 39 | 11 |
| 0021-5 | not tested | not tested |
| 0021-6 | 38 | 12 |
| 0021-7 | 22 | 28 |
| 0021-8 | not tested | not tested |
| 0021-9 | 30 | 20 |
| 0021-10 | 34 | 16 |
| 0022-1 | not tested | not tested |
| 0022-2 | 40 | 10 |
| 0022-3 | 42 | 8 |
| 0022-4 | 39 | 11 |
| 0022-5 | 40 | 10 |
| 0022-6 | 31 | 19 |
| 0022-7 | 39 | 11 |
| 0022-8 | 40 | 10 |
| 0022-9 | 35 | 15 |
| 0022-10 | 35 | 15 |
| 0023-1 | 41 | 9 |
| 0023-2 | not tested | not tested |
| 0023-3 | not tested | not tested |
| 0023-4 | 38 | 12 |
| 0023-5 | 36 | 14 |
| 0023-6 | 40 | 10 |
| 0023-7 | not tested | not tested |
| 0023-8 | not tested | not tested |
| 0023-9 | 39 | 11 |
| 0023-10 | 39 | 11 |
| 0023-11 | 35 | 15 |
| 0023-12 | Not tested | Not tested |
| 0024-1 | 37 | 13 |
| 0024-2 | 42 | 8 |
| 0024-3 | 38 | 12 |
| 0024-4 | 41 | 9 |
| 0024-5 | 39 | 11 |
| 0024-6 | 38 | 12 |
| 0024-7 | Not tested | not tested |
| 0024-8 | 44 | 6 |
| 0024-9 | 38 | 12 |
| 0024-10 | 40 | 10 |
| 0024-11 | 27 | 13 |
| 0025-1 | 30 | 20 |
| 0025-2 | 35 | 15 |
| 0025-3 | 34 | 16 |
| 0025-4 | 32 | 18 |
| 0025-5 | 50 | 0 |
| 0025-6 | 34 | 16 |
| 0025-7 | 37 | 13 |
| 0025-8 | Not tested | not tested |
| 0025-9 | 36 | 14 |
| 0025-10 | Not tested | not tested |
| 0025-11 | Not tested | not tested |
| 0026-1 | 30 | 20 |
| 0026-2 | 31 | 19 |
| 0026-3 | 36 | 14 |
| 0026-4 | 34 | 16 |
| 0026-5 | Not tested | not tested |
| 0026-6 | Not tested | not tested |

Only plant 0025-5 resulted in a non-segregating hybrid. A total of 14 out of 60 lines were marked for low fertility (SNFD phenotype). Segregation of the F₁ population in this table is also compiled in Table 8.

To increase the number of resistant plants, resulting in a non-segregating F₁, a second test was done. Plants, marked for low fertility were not removed before crossing. Results are listed in Table 7, segregation is also compiled in Table 8. A total of 12 out of 50 lines (25%) resulted in a completely resistant F₁ population.

TABLE 7

F₁ segregation of Manito, derived from individual plants (second screening)

| Plant no. of resistant parent | No. of resistant F1 plants | No. of susceptible F1 plants |
|---|---|---|
| 2825-1 | 32 | 18 |
| 2825-2 | 31 | 19 |
| 2826-3 | 35 | 15 |
| 2827-2 | 30 | 20 |
| 2827-3 | 29 | 21 |
| 2827-4 | 24 | 26 |
| 2828-2 | 29 | 21 |
| 2828-3 | 33 | 17 |
| 2829-1 | 28 | 22 |
| 2829-3 | 28 | 22 |
| 2829-4 | 40 | 10 |
| 2829-5 | 33 | 17 |
| 2831-4 | 35 | 15 |
| 2832-1 | 34 | 16 |
| 2832-2 | 34 | 16 |
| 2832-3 | 33 | 17 |
| 2833-1 | 14 | 36 |
| 2833-2 | 32 | 18 |
| 2833-4 | 50 | 0 |
| 2833-5 | 37 | 13 |
| 2825-4 | 50 | 0 |
| 2826-1 | 31 | 19 |
| 2826-2 | 26 | 24 |
| 2826-4 | 50 | 0 |
| 2826-5 | 50 | 0 |
| 2827-1 | 27 | 23 |
| 2827-5 | 50 | 0 |
| 2828-1 | 25 | 25 |
| 2828-4 | 29 | 21 |
| 2829-2 | 17 | 33 |
| 2830-3 | 11 | 39 |
| 2830-4 | 22 | 28 |
| 2831-1 | 24 | 26 |
| 2831-2 | 19 | 31 |
| 2831-3 | 28 | 22 |
| 2832-4 | 29 | 21 |
| 2833-3 | 50 | 0 |
| 2833-6 | 50 | 0 |
| 2834-1 | 24 | 27 |
| 2834-3 | 23 | 27 |
| 2834-4 | 20 | 30 |
| 2834-5 | 50 | 0 |
| 2834-6 | 48 | 2 |
| 2825-3 | 50 | 0 |
| 2830-1 | 20 | 0 |
| 2830-2 | 50 | 0 |
| 2830-5 | 20 | 30 |
| 2831-5 | 50 | 0 |
| 2832-5 | 24 | 26 |
| 2834-2 | 31 | 19 |

TABLE 8

Compiled results of segregating F₁'s in Examples 2 and 3.

| Example | Plant no. of resistant parent | Name | No. of resistant plants | No. of susceptible plants |
|---|---|---|---|---|
| 2 | 4578 | male parent of Sylvia | 214 | 191 |
| 2 | 6636, cross 1 | male parent of Sylvia | 127 | 113 |
| 2 | 6636, cross 2 | male parent of Sylvia | 147 | 103 |
| 3 | 0021-0026 | male parent of Manito | 1602 | 608 |
| 3 | 2825-2834 | male parent of Manito | 1069 | 832 |

Similar in all cases is that there are more resistant than susceptible plants. Segregation with 4578 and 6636-cross 1 is close to 1:1, fitting in single gene model in which the resistant parent is heterozygous. In 6636-cross 2 and 2825-2834 segregation is more close to 9:7. A 9:7 segregation is derived from an $F_2$ population. By crossing two homozygous lines (lines don't segregate for resistance) it is not possible to get 9:7 segregation in the $F_1$. More likely is that also here an 1:1 segregation is present. Segregation of 0021-0026 differs from the others fitting best in an 3:1 segregation. Probably this difference is caused by the fact that plants were selected on fertility and low fertile plants were removed before crossings were made.

Example 4

Linkage Drag as an Explanation for the Observed Non-Mendelian Inheritance of the L4 Allele Introduction Of the plants used for the crossings in table 8, fertility and dwarf growth (SNFD phenotype) were scored. All plants that resulted in a non-segregating $F_1$ showed low fertility. This indicates linkage of low fertility and non-segregation. Results shown in Table 7 showed that around 25% of the plants resulting in a non-segregating hybrid. In Table 6, 25% of the plants were marked as low fertile and removed before evaluation of the F1. When the low fertile plants are considered as good resistance transferring parents then the results between table 6 and table 7 are comparable. As referred to herein inbred lines derived from these non-segregating plants did indeed show dwarf growth. From this it can be concluded that the negative traits (non-stable resistance, low fertility, dwarf growth) are closely linked or pleiotropic to the L4 allele.

Possible explanations of the observations in Example 1-3 on the nature of the segregation in $F_1$ were formulated and tested. The possibility that a lethal gene was linked to the susceptible allele or that a lethal gene was linked to the resistant allele were tested, but rejected. The possibilities of gene silencing, the requirement of a second gene for expression of the L4 allele or the requirement of a second gene for transfer of the L4 allele, were also rejected. Further, no evidence was found for the presence transposons or imprinting (genes are silenced due to specific conditions during seed development). Furthermore, the possibility that the resistance trait was not monogenic was ruled out after elaborate testing schemes. It was subsequently tested whether the introgression segment of *C. chacoense* would result in problems with chromosomal folding of the *C. annuum* chromosome. An irregular folding would result in an imbalanced chromosome, causing problems in the meiosis of the homozygous (L4L4) plants. During chromosome pairing, one of the chromosomes could then become damaged resulting in a defective allele, called "−" allele. This, in turn, would result in loss of resistance. Taken into account that in segregating $F_1$'s no markers were found in susceptible plants, breaking of the chromosome is most likely. If homozygous presence of the defective allele is lethal, selfing of the L4-genotype would indeed result in a complete resistant line in a bioassay. Also, a non-segregating $F_1$ can be derived in this way and when an L4-genotype is crossed with a susceptible line, the $F_1$ will segregate in 1:1 ratio. Plants with homozygous L4 genotype (L4L4) can be found after selfing of an L4-genotype, however it predicted that these plants would encounter problems in the meiosis. This would then explain why a line is completely resistant (i.e. all plants tested are resistant) when tested in a bioassay and is still found to result in a segregating $F_1$ population when crossed with a susceptible parent. It would also explain why no markers were found back in plants of the $F_1$ population that were susceptible.

This explanation predicts that the L4L4 genotype that results in a non-segregating $F_1$ is the result of a re-arrangement of the chromosome folding. In this re-arranged folding situation, chromosome pairing would not result in breaking of a chromosome arm. However, other processes within the plant are most likely disrupted resulting in low fertility and reduced growth (dwarf plants). It is known that only a limited amount of pollen is derived from these plants. Also, low amount of seeds are reportedly derived from such lines.

From the above experiments it was therefore concluded that the fragment of the genome of *C. chacoense* that comprises the L4 allele is too large and causes segregating $F_1$ populations. Therefore, decreasing the size of this segment could solve the problem.

Experimental Setup

Figure 2:
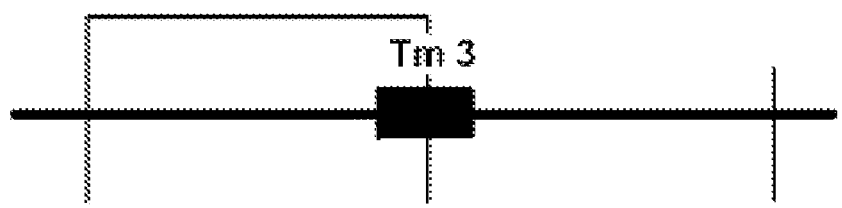
FIG. 2 shows the same micromap wherein the individual markers are indicated.

The presence of various markers of the L4 locus was assessed in a number of pepper lines. First, two resistant *C. annuum* lines, M-873 and M-3751 were evaluated for the size of the introgression segment. These lines were known to result in non-segregating $F_1$'s and normal fertility. The size of the segment was compared to the introgression present in S&G inbred lines (Father of Manito) by screening for markers flanking the L4 allele. For position of the markers, see FIG. 2. Results are listed in Table 9.

Lines are tested on 4 markers linked to the L4-locus, position of the markers towards the L4 allele is shown in table 1. Markers, listed in Table 9, are scored homozygous present, heterozygous present or absent. Also fertility of the resistant parental line and resistance of the $F_1$ is listed. Evaluation of fertility was performed visually, by scoring the amount of pollen into "limited amount of pollen" (−; bad fertility), "intermediate amount of pollen" (+/−; medium fertility), and "amount of pollen similar to a non-resistant, fertile control plant" (+; good fertility).

Resistance in lines M-873 and M-3751 originated from pepper breeding lines of De Ruiter Seeds, Bergschenhoek, The Netherlands. All other sources shared an S&G inbred line as L4 donor. Of the lines M-873 and M-3751 plants with good and medium fertility were screened for the presence or absence of markers. Medium fertility was in al cases better than fertility in Father of Manito lines. Other lines were breeding lines which were selected based on fertility or because they resulted in non-segregating hybrids.

TABLE 9

Evaluations of *C. chacoense* introgressions in several pepper lines.

| | | | | | L4 Marker | | | |
|---|---|---|---|---|---|---|---|---|
| Nr. | plant nr | Fertility | $F_1$ | generation | E39/M58-F-95 | E58/M60-F-255 | E58/M50-F-580 | E39/M58-F-65 |
| M-873 | 1 | + | Resistant | F8 | + | ++ | + | − |
| | 2 | + | Resistant | F8 | + | ++ | + | − |
| | 3 | + | Resistant | F8 | + | ++ | + | − |
| | 4 | ± | Resistant | F8 | + | ++ | + | − |
| | 5 | ± | Resistant | F8 | + | ++ | + | − |
| | 6 | ± | Resistant | F8 | + | ++ | + | − |

TABLE 9-continued

Evaluations of C. chacoense introgressions in several pepper lines.

| | | | | | L4 Marker | | | |
|---|---|---|---|---|---|---|---|---|
| Nr. | plant nr | Fertility | $F_1$ | generation | E39/M58-F-95 | E58/M60-F-255 | E58/M50-F-580 | E39/M58-F-65 |
| M-3751 | 1 | + | Resistant | F4 | + | ++ | + | − |
| | 2 | + | Resistant | F4 | + | ++ | + | − |
| | 3 | + | Resistant | F4 | + | ++ | + | − |
| | 4 | ± | Resistant | F4 | + | ++ | + | − |
| | 5 | ± | Resistant | F4 | + | ++ | + | − |
| | 6 | ± | Resistant | F4 | + | ++ | + | − |
| 8972 | 1 | + | ? | F5 | +/− | + | +/− | +/− |
| | 2 | + | ? | F5 | +/− | + | +/− | +/− |
| | 3 | + | ? | F5 | +/− | + | +/− | +/− |
| | 4 | + | ? | F5 | +/− | + | +/− | +/− |
| 8600 | 9 | −/± | Resistant | F11 | ++ | ++ | + | ++ |
| 8602 | 3 | −/± | Resistant | F11 | ++ | ++ | + | ++ |
| | 5 | −/± | Resistant | F11 | ++ | ++ | + | ++ |
| 8603 | 7 | −/± | Resistant | F11 | ++ | ++ | + | ++ |
| 8607 | 7 | −/± | Resistant | F11 | ++ | ++ | + | ++ |
| 8609 | 2 | −/± | ? | F11 | + | + | +/− | +/− |
| 8613 | 2 | −/± | ? | F11 | + | + | +/− | +/− |
| Mother of Manito | 1 | − | Resistant | F11 | ++ | ++ | + | ++ |

++: marker homozygous present, resistant; −: marker homozygous absent, susceptible; +/−: marker heterozygous present, resistant; +: marker present, allelic differences not tested; ?, not tested.

Results indicate that in the lines M-873 and M-3751 a smaller introgression segment is present. The marker of Group 2 (E39/M58-F-65) is absent. By evaluating the pedigree of these lines, both shared vp-nr 91Pa0424, F3T13 7310 in common.

Plants of lines 8972, 8609 and 8613 gave the score heterozygous, this in spite of a complete resistant score in the bioassay. With line 8972 crossings were made. Results are listed in table 10.

TABLE 10

Results of $F_1$ populations derived from heterozygous scoring line 8972 of Table 9.

| | $F_1$'s with field nr 8972 | |
|---|---|---|
| Plant nr. | No. of resistant plants | No. of susceptible plants |
| 99Pa1256 | 12 | 18 |
| 99Pa1270 | 30 | 0 |
| 99Pa1280 | 13 | 14 |
| 99Pa1285 | 18 | 16 |
| 99Pa1289 | 10 | 14 |

The results of $F_1$ population obtained from line 8972 were according to expectation. To identify further recombinants, segregating lines were analysed for the presence of L4-locus markers. Lines were chosen, based on $F_3$-segregation, which was most close to 3:1. Plants of each $F_3$ population were pooled, as recombination should have occurred during selfing from $F_1$ to $F_2$. In case a recombination had taken place, the $F_3$ population should be homozygous for the recombination. Selected lines are listed in table 11.

TABLE 11

Selected lines for recombinant identification.

| | | segregation | |
|---|---|---|---|
| population | line nr | No. of resistant plants | No. of plants tested |
| 1 | 6552 | 25 | 35 |
| 2 | 6557 | 27 | 35 |
| 3 | 6559 | 32 | 35 |
| 4 | 6561 | 29 | 35 |
| 5 | 6565 | 26 | 35 |
| 6 | 6566 | 25 | 35 |
| 7 | 6567 | 26 | 35 |
| 8 | 6568 | 26 | 35 |
| 9 | 6571 | 35 | 44 |
| 10 | 6572 | 32 | 44 |
| 11 | 6585 | 29 | 44 |

Results of the marker analysis for these plants are listed in table 12. Markers of the L4 locus are indicated as shown in Table 1. Marker score "+" indicates presence of the marker, marker score "−" indicates absence.

TABLE 12

Marker score of selected L4 resistant and non SNFD phenotype lines.

| Marker | Group 1 (L4 allele-specific) | | | Group 1/3 | | Group 3 | Group 2 | |
|---|---|---|---|---|---|---|---|---|
| Plant no. | E58/M50-F-580 | E39/M58-F-95 | E58/M60-F-255 | E66/M49-F-387 | E74/M61-F-385 | E60/M54-F-447 | E39/M58-F-65 | E39/M51-F-380 |
| 001 | + | + | + | + | + | − | − | − |
| 002 | + | + | + | + | + | + | − | − |

TABLE 12-continued

Marker score of selected L4 resistant and non SNFD phenotype lines.

| Marker Plant no. | Group 1 (L4 allele-specific) E58/M50-F-580 | E39/M58-F-95 | E58/M60-F-255 | Group 1/3 E66/M49-F-387 | E74/M61-F-385 | Group 3 E60/M54-F-447 | Group 2 E39/M58-F-65 | E39/M51-F-380 |
|---|---|---|---|---|---|---|---|---|
| 003 | + | + | + | + | + | + | − | − |
| 004 | + | + | + | + | + | + | − | − |
| 005 | + | + | + | + | + | + | − | − |
| 006 | + | + | + | + | + | + | − | − |
| 007 | + | + | + | + | + | + | − | − |
| 008 | + | + | + | + | + | + | − | − |
| 009 | + | + | + | + | + | + | − | − |
| 010 | + | + | + | + | + | − | − | − |
| 011 | + | + | + | + | + | − | − | − |

It can be concluded that no new recombinants were found within these selected lines that contained the markers for the L4 resistance allele (Group 1 markers), but that did not contain genetic material comprising the location of the markers of Group 2. It was found that these lines were resistant, whereas the SNFD phenotype was not observed. It was therefore concluded that the recombinations that led to the loss of the genetic material comprising the location of the markers of Group 2, or of Group 2 and Group 3 resulted in the loss of the SNFD phenotype.

REFERENCES

Alonso E, Garcia-Luque I, de la Cruz A, Wicke B, Avila-Rincon M J, Serra M T, Castresana C, Diaz-Ruiz J R (1991) Nucleotide sequence of the genomic RNA of pepper mild mottle virus, a resistance-breaking tobamovirus in pepper. *J Gen Virol.* 72:2875-84.

Antignus Y, Lachman O, Pearlsman M (2000) A New Strain of Pepper Mild Mottle Virus (PMMV) "Overcoming Resistance Conferred by L4 Alleles," *Phytoparasitica* 28(3):282-283.

Avila-Rincon M J, Ferrero M L, Alonso E, Garcia-Luque I, Diaz-Ruiz J R (1989) "Nucleotide sequences of 5' and 3' non-coding regions of pepper mild mottle virus strain S RNA," *J. Gen. Virol.* 70:3025-3031.

Ben-Chaim A, Grube R C, Lapidot M, Jahn M, Paran I (2001) "Identification of quantitative trait loci associated with resistance to cucumber mosaic virus in *Capsicum annuum,*" *Theoretical and Applied Genetics* 102(8):1213-1220.

Berzal-Herranz A, de la Cruz A, Tenllado F, Diaz-Ruiz J R, Lopez L, Sanz A I, Vaquero C, Serra M T, Garcia-Luque I (1995) "The *capsicum* L3 gene-mediated resistance against the tobamoviruses is elicited by the coat protein," *Virology,* 209:498-505.

Boukema I W, Jansens K, Hofman K (1980) "Strains of TMV and genes for resistance in *Capsicum,*" *Synopsis of the 4th meeting of the Eucarpia Capsicum Working Group,* p. 44-48.

Boukema I W (1982) "Resistance to a new strain of TMV in *Capsicum chacoense* Hunz," *Capsicum Newsletter* 1:49-51.

Boukema I W (1983) "Research on the location of the gene for resistance to TMV in *Capsicum chacoense* Hunz. and male sterility in progenies from the cross *C. chacoense×C. annuum* L.," *Proceedings Vth Meeting Capsicum and Eggplant Working Group of Eucarpia,* 4-7 July, Plovdiv, Bulgaria p. 84-87.

Boukema I W (1984) "Resistance to TMV in *Capsicum chacoense* Hunz. is governed by an allele of the L-locus," *Capsicum Newsletter* 3:47-48.

Briggs F N, Knowles P F (1967) *Introduction to Plant Breeding.* Reinhold Publishing Corporation. U.S.A.

Christou P, Murphy J E, and Swain W F (1987) "Stable transformation of soybean by electroporation and root formation from transformed callus," *Proc. Natl. Acad. Sci. USA* 84:3962-3966.

Dallwitz M J (1980) "A general system for coding taxonomic descriptions," *Taxon* 29:41-46

Dallwitz M J, Paine T A, Zurcher E J (1993) *User's Guide to the DELTA System: a general system for processing taxonomic descriptions,* 4th edition. 136 pp. (CSIRO Division of Entomology: Canberra)

Deshayes A, Herrera-Estrella L, Caboche M (1985) "Liposome-mediated transformation of tobacco mesophyll protoplasts by an *Escherichia coli* plasmid," *EMBO J.* 4:2731-2737.

D'Halluin K, Bonne E, Bossut M, De Beuckeleer M, Leemans J (1992) *Plant. Cell* 4:1495-1505.

Dodds J H and Roberts L W (1995)*Experiments in Plant Tissue Culture.* 3rd Ed. Cambridge University Press.

Draper J, Davey M R, Freeman J P, Cocking E C and Cox B J (1982) "Ti plasmid homologous sequences present in tissues from *Agrobacterium* plasmid-transformed Petunia protoplasts," *Plant and Cell Physiol.* 23:451-458.

Garcia-Luque I, Ferrero M L, Rodriquez J M, Alonso E, de la Cruz A, Sanz A I, Vaquero C, Serra M T, Diaz-Ruiz J R (1993) "The nucleotide sequence of the coat protein genes and 3' non-coding regions of two resistance-breaking tobamoviruses in pepper shows that they are different viruses," *Arch. Virol.* 131(1-2):75-88.

Gilardi P, Garcia-Luque I, Serra M T (2004) "The coat protein of tobamovirus acts as elicitor of both L2 and L4 gene-mediated resistance in *Capsicum,*" *J. Gen. Virol.* 85:2077-2085.

Gleba I U, Sytnik K M, Shoeman R (1984) *Protoplast Fusion, Genetic Engineering in Higher Plants.* Berlin, N.Y.: Springer-Verlag, 1984.

Gruber M Y, Crosby W L (1993) "Vectors for Plant Transformation," *Methods in Plant Molecular Biology & Biotechnology,* Glick B R and Thompson J E (Eds.) CRC Press, pp. 89-119.

Hagiwara K, Ichiki T U, Ogawa Y, Omura T, Tsuda S (2002) "A single amino acid substitution in 126-kDa protein of Pepper mild mottle virus associates with symptom attenuation in pepper; the complete nucleotide sequence of an attenuated strain, C-1421," *Arch Virol.* 147(4):833-840.

Hain R, Stabel P, Czernilofsky A P, Steinbliss H H, Herrera-Estrella L, Schell J (1985) "Uptake, integration, expression and genetic transmission of a selectable chimaeric gene to plant protoplasts," *Mol. Gen. Genet.* 199:161-168.

Horsch R B, Fry J E, Hoffman N L, Eichholts D, Rogers S G, Fraley R T (1985) "A simple method for transferring genes into plants," *Science* 227:1229-1231.

Kado C I (1991) "Molecular mechanisms of crown gall tumorigenesis," *Crit. Rev. Plant Sci.* 10:1-32.

Kirita M, Akutsu K, Watanabe Y, Tsuda S (1997) "Nucleotide sequence of the Japanese isolate of pepper [*Capsicum annuum*] mild mottle tobamovirus (TMV-P) RNA," *Ann. Phytopathol. Soc. Jpn.* 63:373-376.

Klein T M, Gradziel T, Fromm M E, Sanford J C (1988) "Factors influencing gene delivery into *zea mays* cells by high velocity microprojectiles," *Biotechnology* 6:559-563.

Klein T M, Arentzen R, Lewis P A, and Fitzpatrick-McElligott S (1992) "Transformation of microbes, plants and animals by particle bombardment," *Bio/Technology* 10:286-291.

Koop H-U and Spangenberg G (1989) "Electric field induced fusion and cell reconstitution with preselected single protoplasts and subprotoplasts of higher plants," *Electroporation and Electrofusion in Cell Biology*, Neumann, E., Sowers, A. and Wolford, S. (eds), Plenum Publishers, New York, pp. 355-366.

Laursen C M, Krzyzek R A, Flick C E, Anderson P C, Spencer T M (1994) Production of fertile transgenic maize by electroporation of suspension culture cells. Plant Mol Biol. 24(1):51-61.

Lefebvre V, Pflieger S, Thabuis A, Caranta C, Blattes A, Chauvet J C, Daubeze A M, Palloix A (2002) "Towards the saturation of the pepper linkage map by alignment of three intraspecific maps including known-function genes." *Genome* 45(5):839-854.

Lefebvre V, Chevre A M (1995) "Tools for marking plant disease and pest resistance genes: a review," *Agronomie* 15:3-19.

Lim P O, Ryu J S, Lee H J, Lee U, Park Y S, Kwak J M, Choi J K, Nam H G (1997) "Resistance to tobamoviruses in transgenic tobacco plants expressing the coat protein gene of pepper mild mottle virus (Korean isolate)," *Mol Cells.* 7(3):313-319.

Miki B L, Fobert P F, Charest P J, Iyer V N (1993) "Procedures for Introducing Foreign DNA into Plants," *Methods in Plant Molecular Biology & Biotechnology*, Glick B R and Thompson J E (Eds.) CRC Press, pp. 67-88.

Moloney M M, Walker J M, Sharma K K (1989) "High efficiency transformation of *Brassica napus* using *Agrobacterium* vectors," *Plant Cell Reports* 8:238-242.

McKinney H H (1952) "Two strains of tobacco mosaic virus, one of which is seed borne in an etch-immune pungent pepper," *Plant Dis. Rep.,* 36: 184-187.

Michelmore R W (1995) "Molecular approaches to manipulation of disease resistance genes," *Ann. Rev. Phytopathol.* 15:393-427.

Phillips R L, Somers D A, Hibberd K A (1988) "Cell/tissue culture and in vitro manipulation," *Corn and corn improvement,* 3rd ed., pp. 345-387. G. F. Sprague & J. W. Dudley (Eds.) Madison, Wis., USA, American Society of Agronomy.

Rast A T B (1988) "Pepper tobamoviruses and pathotypes used in resistance breeding," *Capsicum Newsletter,* 7:20-23.

Rieger R, Michaelis A, Green M M (1968) *A Glossary of Genetics and Cytogenetics*, Springer-Verlag, N.Y.

Rodriguez-Cerezo E, Moya A, Garcia-Arenal F (1989) "Variability and evolution of the plant RNA virus pepper mild mottle virus," *J. Virol.* 63(5):2198-2203.

Ruiz del Pino M, Moreno A, Garcia de Lacoba M, Castillo-Lluva S, Gilardi P, Serra M T, Garcia-Luque I (2003) "Biological and molecular characterization of P101 isolate, a tobamoviral pepper strain from Bulgaria," *Arch. Virol.* 148(11):2115-2135.

Sanford J C, Klein T M, Wolf E D, Allen N (1987) "Delivery of substances into cells and tissues using a particle bombardment process," *J. Particulate Sci. Technol.* 5:27-37.

Sanford J C (1988) "The biolistic process," *Trends in Biotechnology* 6:299-302.

Sanford J C (1990) "Biolistic plant transformation," *Physiologica Plantarum,* 79:206-209.

Sanford J C, Smith F D, and Russell J A (1993) "Optimizing the biolistic process for different biological applications," *Methods in Enzymology* 217:483-509.

Sundberg E and Glimelius K (1986) "A method for production of interspecific hybrids within Brassicaceae via somatic hybridisation, using resynthesis of *Brassica napus* as a model," *Plant Science* 43:158-162.

Tenllado F, Garcia-Luque I, Serra M T, Diaz-Ruiz J R (1996) "Resistance to pepper mild mottle tobamovirus conferred by the 54-kDa gene sequence in transgenic plants does not require expression of the wild-type 54-kDa protein," *Virology* 219(1):330-335.

Tenllado F, Garcia-Luque I, Serra M T, Diaz-Ruiz J R (1997) "Pepper resistance-breaking tobamoviruses: can they coexist in single pepper plants?" *Europ. J. Plant Pathol.* 103(3):235-243.

Tobias I, Rast A T B, Maat D Z (1982) "Tobamoviruses of pepper, eggplant, and tobacco: comparative host reactions and serological relationships," *Neth. J. Plant Pathol.* 88:257-268.

Tsuda S, Kirita M, Watanabe Y (1998) "Characterization of a pepper mild mottle tobamovirus strain capable of overcoming the L3 gene-mediated resistance, distinct from the resistance-breaking Italian isolate," *Mol. Plant Microbe Interact.* 11(4):327-331.

Velasco L, Janssen D, Ruiz-Garcia L, Segundo E, Cuadrado I M (2002) "The complete nucleotide sequence and development of a differential detection assay for a pepper mild mottle virus (PMMoV) isolate that overcomes L3 resistance in pepper," *J. Virol. Methods.* 106(1):135-140.

Van Duin P J W (1998) *Xth EUCARPIA Meeting on Genetics and Breeding of Capsicum & Eggplant*, Avignon, France.

Vos P, Hogers R, Bleeker M, Reijans M, van de Lee T, Hornes M, Frijters A, Pot J, Peleman J, Kuiper M (1995) "AFLP: a new technique for DNA fingerprinting," *Nucleic Acids Res.* 23:4407-4414.

Werner R, Olschewski J, Mergenhagen D (2001) "Identification and cloning of amplified fragment length polymorphism markers linked to the mating type locus of *Chlamydomonas reinhardtii* (*Chlorophyta*)," *J. Phycol.* 37(3):427.

Wetter C, Conti M, Altschuh D, Tabillion R, van Regenmortel M H V (1984) "Pepper mild mottle virus, a tobamovirus infecting pepper cultivars in Sicily," *Phytopathology* 74:405-410.

Winter P, Kahl G (1995) "Molecular marker technologies for plant improvement," *World Journal of Microbiology and Biotechnology* 11:438-448.

Zhang L, Cheng L, Xu N, Zhao M, Li C, Yuan J, and Jia S (1991) "Efficient transformation of tobacco by ultrasonication," *Biotechnology* 9:996-997.

The invention claimed is:

1. An inbred plant of the *Capsicum* genus that exhibits resistance to pepper mild mottle virus (PMMoV) pathotype 1.2.3 due to the presence of the L4 resistance allele in the genome of said plant, wherein said L4 resistance allele is truncated, and wherein the truncation involves the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one Group 2 marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of the Group 3 marker E60/M54-F-447, and wherein said plant is homozygous for said L4 resistance allele.

2. The plant according to claim 1, wherein said L4 resistance allele is derived from the genome of *C. chacoense*.

3. The plant according to claim 1, wherein said plant is a white flowering *Capsicum*.

4. The plant according to claim 3, wherein said white flowering *Capsicum* plant is a *C. annuum* plant.

5. The plant according to claim 1, wherein the truncation further involves the absence of at least one Group 1/3 marker selected from the group consisting of E63/M61-F-501, E66/M43-F-387, E66/M49-F-387, E66/M61-F-99, E67/M50-F-150, E67/M62-F-214, E70/M54-F-133, E71/M47-F-550, E74/M61-F-385 as shown in FIG. 3.

6. A hybrid pepper plant that exhibits resistance to PMMoV pathotype 1.2.3, obtainable by crossing the plant according to claim 1 with a homozygous pepper plant that exhibits commercially desirable characteristics, wherein the hybrid plant comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of the Group 3 marker E60/M54-F-447.

7. A method of producing a plant of the *Capsicum* genus that exhibits resistance to PMMoV pathotype 1.2.3, comprising the steps of:
 a) providing a recipient plant of the *Capsicum* genus that is susceptible to PMMoV pathotype 1.2.3 or a part thereof;
 b) providing a donor plant of the *Capsicum* genus that exhibits resistance to PMMoV pathotype 1.2.3 due to the presence of the L4 resistance allele in the genome of said plant;

c) crossing said recipient and donor plant to produce progeny plants that exhibit resistance to PMMoV pathotype 1.2.3, d) screening the genome of resistant progeny plants for the presence of a truncated L4 resistance allele wherein said allele comprises genetic information that confers resistance to PMMoV pathotype 1.2.3 to said progeny plant, wherein the truncation involves the presence of at least one Group 1 marker selected from the group consisting of E58/M50-F-580, E39/M58-F-95, E58/M60-F-255 and E54/M55-F-101, the truncation further comprising a genetic deletion of about 2 cM or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447 and wherein genetic information that confers the SNFD phenotype is absent from said truncated L4 resistance allele at least to such an extent that the SNFD phenotype is not expressed, and selecting a progeny plant that has a truncated L4 resistance allele.

8. The method according to claim 7, wherein the screening in step d) is performed by screening the genome of said progeny plant in addition for the absence of at least one Group 1/3 marker selected from the group consisting of E63/M61-F-501, E66/M43-F-387, E66/M49-F-387, E66/M61-F-99, E67/M50-F-150, E67/M62-F-214, E70/M54-F-133, E71/M47-F-550, E74/M61-F-385 as shown in FIG. 3.

9. The method according to claim 7, wherein the screening in step d) is performed by screening the genome of said progeny plant for the presence of at least one marker of the L4 resistance allele selected from the group consisting of markers E39/M58-F-95, E54/M55-F-101, E58/M60-F-255 and E58/M50-F-580.

10. The method according to claim 7, wherein said step c) comprises performing a resistance bioassay.

11. The method according to claim 7, wherein said progeny plant is a plant of a segregating population produced by self-pollination of an $F_1$ plant obtained from said cross in step c), or by crossing an $F_1$ plant obtained from said cross with another pepper plant.

12. A method for producing an inbred plant of the *Capsicum* genus that exhibits resistance to PMMoV pathotype 1.2.3, comprising performing the method according to claim 7 and further performing the steps of:

e) selfing the selected plants;

f) planting seed obtained from said selfing and growing said seed into plants;

g) identifying plants from step g) that exhibit PMMoV pathotype 1.2.3 resistance and possess commercially desirable characteristics, and h) repeating steps e)-g) until an inbred pepper plant is produced that exhibits PMMoV pathotype 1.2.3 resistance and possesses commercially desirable characteristics.

13. The method according to claim 7, wherein said donor plant is a *C. chacoense* plant or wherein said truncated L4 resistance allele is derived from the genome of *C. chacoense.*

14. The method according to claim 7, wherein said recipient plant is a *C. annuum* plant.

15. A plant of the *Capsicum* genus that exhibits resistance to PMMoV pathotype 1.2.3 obtainable by the method according to claim 7.

16. The plant according to claim 15, wherein said plant is an inbred plant.

17. A progeny of the plant according to claim 1, wherein the progeny comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

18. A part or derivative of the plant according to claim 1 suitable for propagation, selected from the group consisting of leaves, stems, roots, shoots, fruits and the like, protoplasts, somatic embryos, anthers, petioles, cells in culture, seeds and the like, the part or derivative comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

19. Part or derivative of the plant according to claim 1 suitable for consumption, the part or derivative comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

20. A pepper seed produced by crossing the *Capsicum* plant according to claim 1 with a *Capsicum* plant that exhibits commercially desirable characteristics or by selfing the *Capsicum* plant according to claim 1, said seed comprising a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

21. A hybrid pepper plant, or part thereof, that exhibits resistance to PMMoV pathotype 1.2.3, obtainable by crossing the plant of claim 16 with a homozygous pepper plant that exhibits commercially desirable characteristics, said hybrid pepper plant or part thereof comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

22. The plant according to claim 1, wherein the L4 resistance allele is selected by the absence of at least one Group 2 marker selected from the group consisting of E35/M49-F-90, E39/M58-F-65, E39/M51-F-380, E58/M62-F-168, E66/M54-F-600, and Tm3-DRS as shown in FIG. 3.

23. The hybrid pepper plant according to claim 6 wherein the homozygous pepper plant is inbred.

24. The method according to claim 8, wherein the L4 resistance allele is selected by the absence of at least one Group 2 marker selected from the group consisting of E35/M49-F-90, E39/M58-F-65, E39/M51-F-380, E58/M62-F-168, E66/M54-F-600, and Tm3-DRS as shown in FIG. 3.

25. The hybrid pepper plant or part thereof according to claim 21 wherein the homozygous pepper plant is inbred.

26. The part or derivative according to claim 19, which is a fruit.

27. A part or derivative of the hybrid pepper plant according to claim 6 suitable for propagation, selected from the group consisting of leaves, stems, roots, shoots, fruits, protoplasts, somatic embryos, anthers, petioles, cells in culture, seeds, the part or derivative comprises a truncated L4 resistance allele, the truncation involving the presence of at least one Group 1 marker selected from the group consisting of E58/M50-F-580, E39/M58-F-95, E58/M60-F-255 and E54/M55-F-101, the truncation further comprising a genetic deletion of about 2 centimorgans (cM) or less between a Group 2 marker and a Group 1 marker involving the absence of at least one marker selected from the group consisting of E35/M49-F-90, E39/M58-F-65, E39/M51-F-380, E58/M62-F-168, E66/M54-F-600, and Tm3-DRS, or wherein the truncation comprises a genetic deletion of about 2 cM or less between a Group 3 marker and a Group 1 marker, involving the absence of E60/M54-F-447.

* * * * *

SEQUENCE LISTING

<160> NUMBER OF SEQ ID NOS: 30

<210> SEQ ID NO 1
<211> LENGTH: 16
<212> TYPE: DNA
<213> ORGANISM: Artificial Aequence
<220> FEATURE:
<223> OTHER INFORMATION: Primer (core sequence)

<400> SEQUENCE: 1
gactgcgtac caattc                                                   16

<210> SEQ ID NO 2
<211> LENGTH: 16
<212> TYPE: DNA
<213> ORGANISM: Artificial Sequence
<220> FEATURE:
<223> OTHER INFORMATION: Primer (core sequence)

<400> SEQUENCE: 2
gatgagtcct gagtaa                                                   16

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
aatccttcaa ctgccatttc                                               20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
attgggacat gaggtgtgta                                               20

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
gactgcgtac caattcaga                                                19

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
gactgcgtac caattccct                                                19

<210> SEQ ID NO 7
<211> LENGTH: 19
<212> TYPE: DNA

```
<213> ORGANISM: Artificial Sequence
<220> FEATURE:
<223> OTHER INFORMATION: PCR primer

<400> SEQUENCE: 7
gactgcgtac caattccgt                                                    19

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
gatgagtcct gagtaacgt                                                    19

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
gatgagtcct gagtaacga                                                    19

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
gatgagtcct gagtaactc                                                    19

<210> SEQ ID NO 11
<211> LENGTH: 19
<212> TYPE: DNA
<213> ORGANISM: Artificial Sequence
<220> FEATURE:
<223> OTHER INFORMATION: PCR primer

<400> SEQUENCE: 11
gatgagtcct gagtaacat                                                    19

<210> SEQ ID NO 12
<211> LENGTH: 19
<212> TYPE: DNA
<213> ORGANISM: Artificial Sequence
<220> FEATURE:
<223> OTHER INFORMATION: PCR primer

<400> SEQUENCE: 12
gactgcgtac caattcaca                                                    19

<210> SEQ ID NO 13
<211> LENGTH: 19
<212> TYPE: DNA
<213> ORGANISM: Artificial Sequence
<220> FEATURE:
<223> OTHER INFORMATION: PCR primer

<400> SEQUENCE: 13
gactgcgtac caattcaga                                                    19
```

<210> SEQ ID NO 14
<211> LENGTH: 19
<212> TYPE: DNA
<213> ORGANISM: Artificial Sequence
<220> FEATURE:
<223> OTHER INFORMATION: PCR primer

<400> SEQUENCE: 14
gactgcgtac caattcgat                                                19

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
aatccttcaa ctgccatttc                                               20

<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
gatgagtcct gagtaacag                                                19

<210> SEQ ID NO 17
<211> LENGTH: 19
<212> TYPE: DNA
<213> ORGANISM: Artificial Sequence
<220> FEATURE:
<223> OTHER INFORMATION: PCR primer

<400> SEQUENCE: 17
gatgagtcct gagtaacgt                                                19

<210> SEQ ID NO 18
<211> LENGTH: 19
<212> TYPE: DNA
<213> ORGANISM: Artificial Sequence
<220> FEATURE:
<223> OTHER INFORMATION: PCR primer

<400> SEQUENCE: 18
gatgagtcct gagtaacca                                                19

<210> SEQ ID NO 19
<211> LENGTH: 19
<212> TYPE: DNA
<213> ORGANISM: Artificial Sequence
<220> FEATURE:
<223> OTHER INFORMATION: PCR primer

<400> SEQUENCE: 19
gatgagtcct gagtaactt                                                19

<210> SEQ ID NO 20
<211> LENGTH: 19
<212> TYPE: DNA
<213> ORGANISM: Artificial Sequence
<220> FEATURE:
<223> OTHER INFORMATION: PCR primer

```
<400> SEQUENCE: 20
gatgagtcct gagtaacct                                            19

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
attgggacat gaggtgtgta                                           20

<210> SEQ ID NO 22
<211> LENGTH: 19
<212> TYPE: DNA
<213> ORGANISM: Artificial Sequence
<220> FEATURE:
<223> OTHER INFORMATION: PCR primer

<400> SEQUENCE: 22
gactgcgtac caattcctc                                            19

<210> SEQ ID NO 23
<211> LENGTH: 19
<212> TYPE: DNA
<213> ORGANISM: Artificial Sequence
<220> FEATURE:
<223> OTHER INFORMATION: PCR primer

<400> SEQUENCE: 23
gactgcgtac caattcgaa                                            19

<210> SEQ ID NO 24
<211> LENGTH: 19
<212> TYPE: DNA
<213> ORGANISM: Artificial Sequence
<220> FEATURE:
<223> OTHER INFORMATION: PCR primer

<400> SEQUENCE: 24
gactgcgtac caattcgca                                            19

<210> SEQ ID NO 25
<211> LENGTH: 19
<212> TYPE: DNA
<213> ORGANISM: Artificial Sequence
<220> FEATURE:
<223> OTHER INFORMATION: PCR primer

<400> SEQUENCE: 25
gactgcgtac caattcgct                                            19

<210> SEQ ID NO 26
<211> LENGTH: 19
<212> TYPE: DNA
<213> ORGANISM: Artificial Sequence
<220> FEATURE:
<223> OTHER INFORMATION: PCR primer

<400> SEQUENCE: 26
gactgcgtac caattcgga                                            19

<210> SEQ ID NO 27
<211> LENGTH: 19
<212> TYPE: DNA
```

```
<213> ORGANISM: Artificial Sequence
<220> FEATURE:
<223> OTHER INFORMATION: PCR primer

<400> SEQUENCE: 27
gactgcgtac caattcggt                                                  19

<210> SEQ ID NO 28
<211> LENGTH: 19
<212> TYPE: DNA
<213> ORGANISM: Artificial Sequence
<220> FEATURE:
<223> OTHER INFORMATION: PCR primer

<400> SEQUENCE: 28
gatgagtcct gagtaactg                                                  19

<210> SEQ ID NO 29
<211> LENGTH: 19
<212> TYPE: DNA
<213> ORGANISM: Artificial Sequence
<220> FEATURE:
<223> OTHER INFORMATION: PCR primer

<400> SEQUENCE: 29
gatgagtcct gagtaaata                                                  19

<210> SEQ ID NO 30
<211> LENGTH: 19
<212> TYPE: DNA
<213> ORGANISM: Artificial Sequence
<220> FEATURE:
<223> OTHER INFORMATION: PCR primer

<400> SEQUENCE: 30
gatgagtcct gagtaacaa                                                  19
```